(12) United States Patent
Okamoto et al.

(10) Patent No.: US 8,409,079 B2
(45) Date of Patent: Apr. 2, 2013

(54) ELECTRIC BENDING OPERATION DEVICE AND MEDICAL TREATMENT SYSTEM INCLUDING ELECTRIC BENDING OPERATION DEVICE

(75) Inventors: Yasuhiro Okamoto, Hachioji (JP); Kazuo Banju, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1343 days.

(21) Appl. No.: 12/120,478

(22) Filed: May 14, 2008

(65) Prior Publication Data

US 2009/0287055 A1   Nov. 19, 2009

(51) Int. Cl.
*A61B 1/00* (2006.01)
*A61B 1/04* (2006.01)
(52) U.S. Cl. .................. 600/146; 600/127; 600/152
(58) Field of Classification Search .............. 600/118, 600/127, 146, 152
See application file for complete search history.

(56) References Cited

U.S. PATENT DOCUMENTS

| | | | |
|---|---|---|---|
| 5,159,446 A | 10/1992 | Hibino et al. | |
| 6,569,084 B1 | 5/2003 | Mizuno et al. | |
| 7,871,371 B2 * | 1/2011 | Komiya et al. | 600/131 |
| 2003/0212308 A1 | 11/2003 | Bendall | |
| 2007/0100201 A1 | 5/2007 | Komiya et al. | |

FOREIGN PATENT DOCUMENTS

| | | |
|---|---|---|
| CN | 1957836 A | 5/2007 |
| DE | 10 2004 007 935 A1 | 5/2005 |
| EP | 1 782 744 A2 | 5/2007 |
| JP | 07-149106 | 6/1995 |
| JP | 3144559 | 1/2001 |
| JP | 2001-278543 | 10/2001 |
| WO | WO 2005/099558 A1 | 10/2005 |

OTHER PUBLICATIONS

Japanese Patent No. 3144559 dated Jan. 5, 2001, together with English-language abstract only of Japanese Patent Application Laid-Open No. 04-150827 dated May 25, 1992.
Japanese Patent Application Laid-Open No. 2001-278543 dated Oct. 10, 2001, together with English-language abstract; and.
Japanese Patent Application Laid-Open No. 07-149106 dated Jun. 13, 1995, together with English-language abstract.
Only of Japanese Patent Application Laid-Open No. 04-150827 dated May 25, 1992.
European Search Report dated Oct. 22, 2009.

* cited by examiner

*Primary Examiner* — Philip R Smith
*Assistant Examiner* — Rynae Boler
(74) *Attorney, Agent, or Firm* — Scully, Scott, Murphy & Presser, P.C.

(57) ABSTRACT

An electric bending operation device can be mounted to an insertion portion of a medical instrument for observation including an electric bending portion. The electric bending operation device may include: an insertion portion mounting mechanism; a rotation mechanism; an insertion portion operation section; and a support column.

8 Claims, 13 Drawing Sheets

ELECTRIC BENDING OPERATION DEVICE AND MEDICAL TREATMENT SYSTEM INCLUDING ELECTRIC BENDING OPERATION DEVICE

BACKGROUND OF THE INVENTION

1. Field of the Invention

The present invention relates to an electric bending operation device having a bending portion operation section that performs bending operation of an electric bending portion provided in an insertion portion of a medical instrument for observation.

2. Description of Related Art

In recent years, medical endoscopes have been used that can observe diseased parts in the body by inserting an elongated insertion portion into the body, and perform various treatments using a treatment instrument passed through a treatment instrument channel if required.

An endoscope includes, on a distal end side of an insertion portion, a bending portion that bends, for example, vertically and laterally, for smoothly inserting the endoscope into a bending region and directing an observation optical system provided at a distal end portion of the endoscope in a desired direction. The bending portion generally bends by an operator rotating a bending knob provided on an operation portion to pull an angle wire. Specifically, the endoscope includes a manually operated bending mechanism.

On the other hand, Japanese Patent No. 3144559 discloses an electric bending endoscope apparatus. With the electric bending endoscope apparatus, bending instruction means such as a joystick provided on an operation portion is tilted to drive a bending motor and pull an angle wire, and thus a bending portion bends in an operation direction of the joystick.

US Patent Application Publication No. 2007-0100201A1 discloses an endoscope system that allows an operator to easily operate various functions of a treatment instrument passed through a treatment instrument channel of an endoscope or various functions of the endoscope while grasping an insertion portion of the endoscope. With the endoscope system, the operator can operate a bending knob by a hand grasping an operation portion of the endoscope, and can operate an operation instruction device by a hand grasping the insertion portion to perform various functions of the endoscope and the treatment instrument besides operating the insertion portion.

Providing the joystick in Japanese Patent No. 3144559 in the operation instruction device of the US Patent Application Publication No. 2007-0100201A1 allows an operator to operate the operation instruction device to perform various functions of the endoscope and the treatment instrument, and perform bending operation of a bending portion. Specifically, the operation instruction device and the electric bending endoscope apparatus are conceivably combined to improve operability.

SUMMARY OF THE INVENTION

An electric bending operation device according to the present invention can be mounted to an insertion portion of a medical instrument for observation including an electric bending portion. The electric bending operation device includes: an insertion portion mounting mechanism; a rotation mechanism; an insertion portion operation section; and a support column.

The insertion portion mounting mechanism includes an insertion portion pressing member that is provided integrally with a rotary cylinder through which the insertion portion is passed and presses and holds the insertion portion. The insertion portion mounting mechanism can be switched between a state where the insertion portion pressing member presses the insertion portion and the rotary cylinder is integral with the insertion portion and a state where the insertion portion is advanced or retracted with respect to the rotary cylinder. The rotation mechanism is provided in the insertion portion mounting mechanism, and rotates the rotary cylinder to rotate the insertion portion around an axis thereof when the rotary cylinder is integral with the insertion portion. The insertion portion operation section includes a bending portion operation section that performs bending operation of the electric bending portion provided in the insertion portion, and a twisting operation portion that rotates the rotary cylinder. The support column integrally connects the insertion portion operation section and the insertion portion mounting mechanism.

The above and other objects, features and advantages of the invention will become more clearly understood from the following description referring to the accompanying drawings.

DETAILED DESCRIPTION OF PREFERRED EMBODIMENTS

Now, embodiments of the present invention will be described with reference to the drawings.

Figure 1:
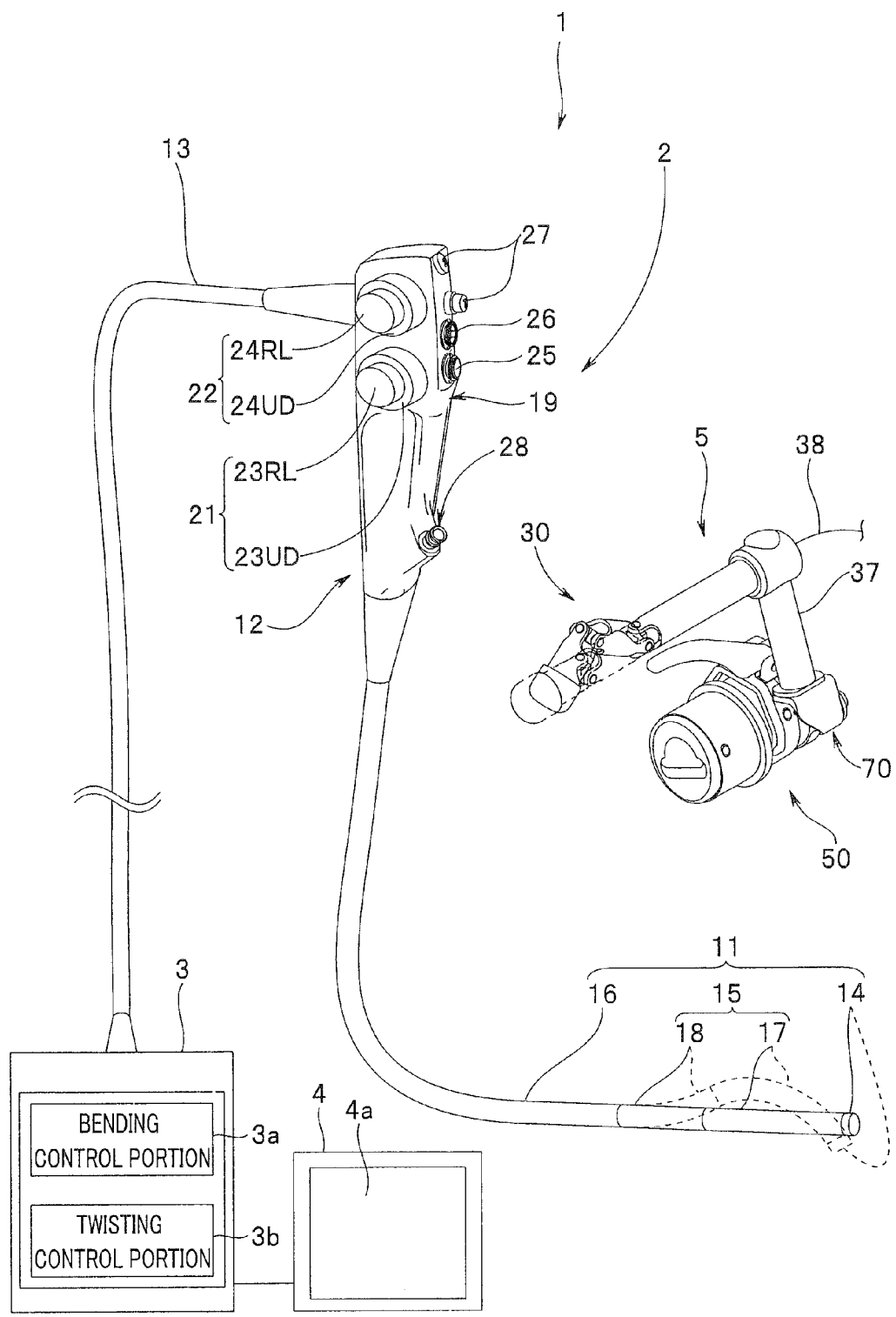
FIG. 1 illustrates an endoscope system including an electric bending endoscope and an electric bending operation device.

As shown in FIG. 1, an endoscope system 1 according to the present embodiment includes an electric bending endoscope 2, an endoscope control device 3, a display device 4, and an electric bending operation device 5.

The electric bending endoscope 2 is a medical instrument for observation, and includes an insertion portion 11 inserted into the body, an operation portion 12 provided on a proximal end side of the insertion portion 11, and a universal cord 13 extending from the operation portion 12. A proximal end portion of the universal cord 13 is connected to the endoscope control device 3. The endoscope control device 3 includes an illumination portion, an image processing portion, control portions 3a and 3b, or the like. The illumination portion includes a power supply that supplies electric power to an illumination lamp that emits illumination light from an illumination window in a distal end portion 14 described later of the electric bending endoscope 2 or a light emitting device such as an LED. The image processing portion includes a drive circuit that drives a solid-state image pickup device such as a CCD or a CMOS included in a distal end portion, an image processing circuit that generates video signals from image signals photoelectrically converted by the solid-state image pickup device and transmitted, or the like. The video signals generated by the image processing circuit in the image processing portion are outputted to the display device 4, and endoscope images are displayed on a screen 4a.

The insertion portion 11 includes the distal end portion 14, an electric bending portion 15, and a flexible tube 16 connected in order from a distal end side. The electric bending portion 15 in the present embodiment includes, for example, a first bending portion 17 and a second bending portion 18. The first bending portion 17 and the second bending portion 18 include a plurality of bending pieces (not shown) connected pivotably in a predetermined direction and bend vertically and laterally. In top, bottom, left and right positions of a distal end piece (not shown) at the most distal end of each of the bending portions 17 and 18, distal end portions of top, bottom, left and right angle wires are secured.

In the present embodiment, the electric bending portion 15 includes the first bending portion 17 and the second bending portion 18 that bend vertically and laterally. However, the electric bending portion 15 is not limited to the configuration, but may include only a first bending portion 17, include a second bending portion 18 that bends vertically, or include a third bending portion that bends vertically and laterally or bends vertically.

The operation portion 12 also serves as a grasping portion grasped by an operator, or a holding portion held by a scope holder (reference numeral 127 in FIG. 9) that constitutes a support base (reference numeral 120 in FIG. 9) described later.

On one side surface or the other side surface of the operation portion 12, a first bending portion operation section 21 and a second bending portion operation section 22 are arranged. The first bending portion operation section 21 includes, for example, a first vertically bending knob 23UD and a first laterally bending knob 23RL coaxially and rotatably provided. The second bending portion operation section 22 includes a second vertically bending knob 24UD and a second laterally bending knob 24RL coaxially and rotatably provided.

The vertical knobs 23UD and 24UD are rotated clockwise when seen from the operator, causing the bending portions 17 and 18 to bend, for example, downward, and the vertical knobs 23UD and 24UD are rotated counterclockwise, causing the bending portions 17 and 18 to bend upward. On the other hand, the lateral knobs 23RL and 24RL are rotated clockwise, causing the bending portions 17 and 18 to bend rightward, and the lateral knobs 23RL and 24RL are rotated counterclockwise, causing the bending portions 17 and 18 to bend leftward.

On a longitudinal side surface 19 between one side surface and the other side surface, an air/water feeding button 25, a suction button 26, and a plurality of buttons 27 for various operations such as display switching of the display device 4, freeze instructions of display images, or release instructions. The operation portion 12 has a treatment instrument insertion opening 28 through which a treatment instrument is introduced into a treatment instrument channel.

The operation portion 12 of the electric bending endoscope 2 includes, for example, a first vertically bending motor (not shown), a first laterally bending motor (not shown), a second vertically bending motor (not shown), and a second laterally bending motor (not shown). The first vertically bending motor pulls and loosens the top angle wire and the bottom angle wire of the first bending portion 17. The first laterally bending motor pulls and loosens the left angle wire and the right angle wire of the first bending portion 17. On the other hand, the second vertically bending motor pulls and loosens the top angle wire and the bottom angle wire of the second bending portion 18. The second laterally bending motor pulls and loosens the left angle wire and the right angle wire of the second bending portion 18.

In the operation portion 12, an unshown knob encoder is provided that detects the directions and the amounts of rotation of the knobs 23UD, 23RL, 24UD and 24RL. When the operator rotates the knobs 23UD, 23RL, 24UD and 24RL clockwise or counterclockwise, the knob encoder outputs knob rotation control signals for indicating the direction and the amount of rotation of each knob to the bending control portion 3a that is a first drive control portion of the endoscope control device 3.

Simultaneously with an input of a rotation control signal, the bending control portion 3a calculates the amount of pull of an angle wire by a wire drive motor corresponding to the rotation control signal and outputs a bending control signal to the corresponding wire drive motor. Then, the wire drive motor corresponding to the operator's knob operation is driven, causing bending operation of the electric bending portion 15.

The electric bending operation device 5 is mounted to the insertion portion 11 of the electric bending endoscope 2 for use. The electric bending operation device 5 includes an insertion portion operation section 30 and an insertion portion mounting mechanism 50, and the insertion portion mounting mechanism 50 includes a rotation mechanism 70. Reference numeral 37 denotes a support column, which integrally connects the insertion portion operation section 30 and the insertion portion mounting mechanism 50.

Figure 2:
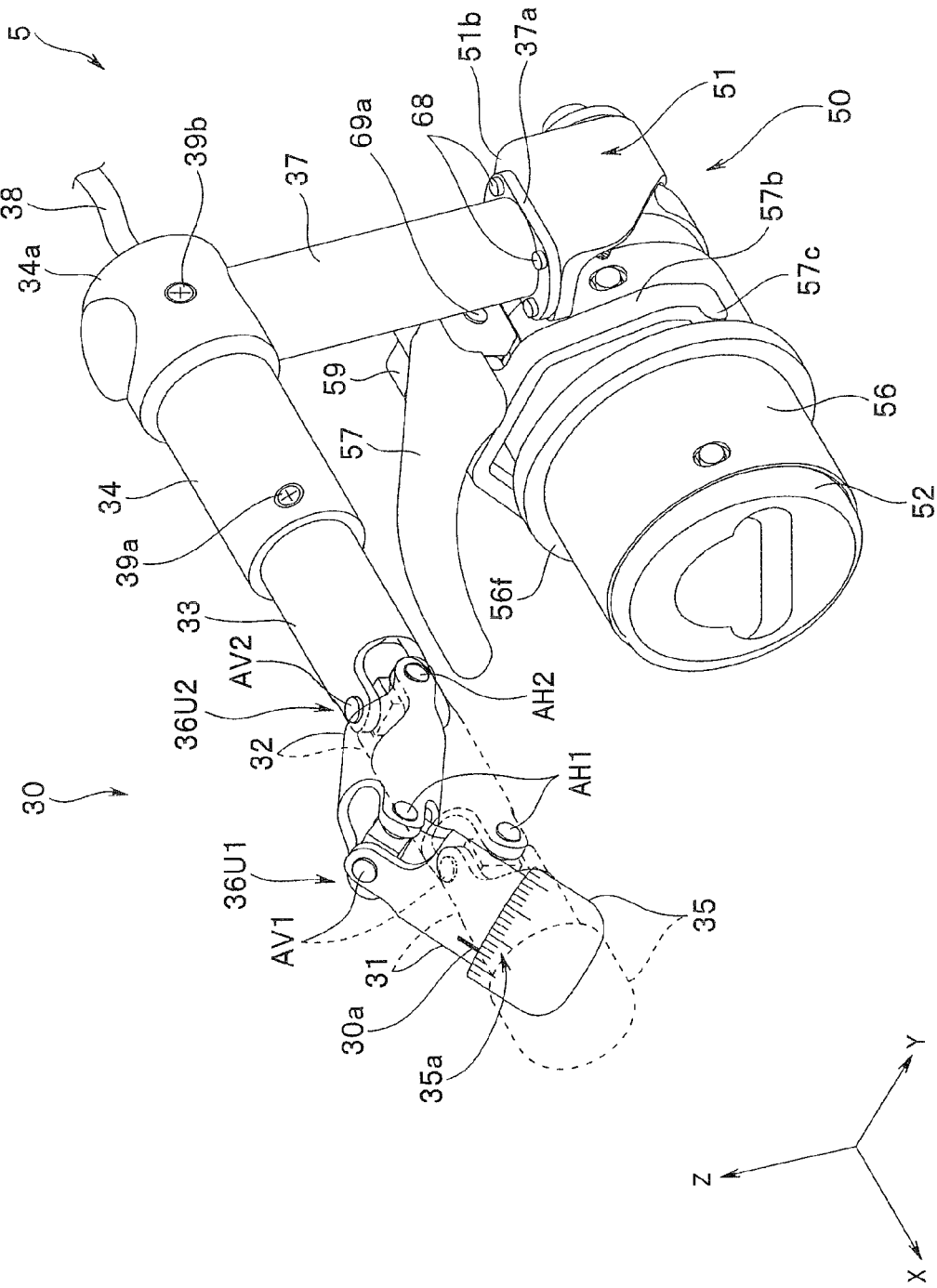
FIG. 2 is a perspective view for illustrating the electric bending operation device that can perform operation of an electric bending portion and twisting operation of an insertion portion provided in the electric bending endoscope.
Figure 3:
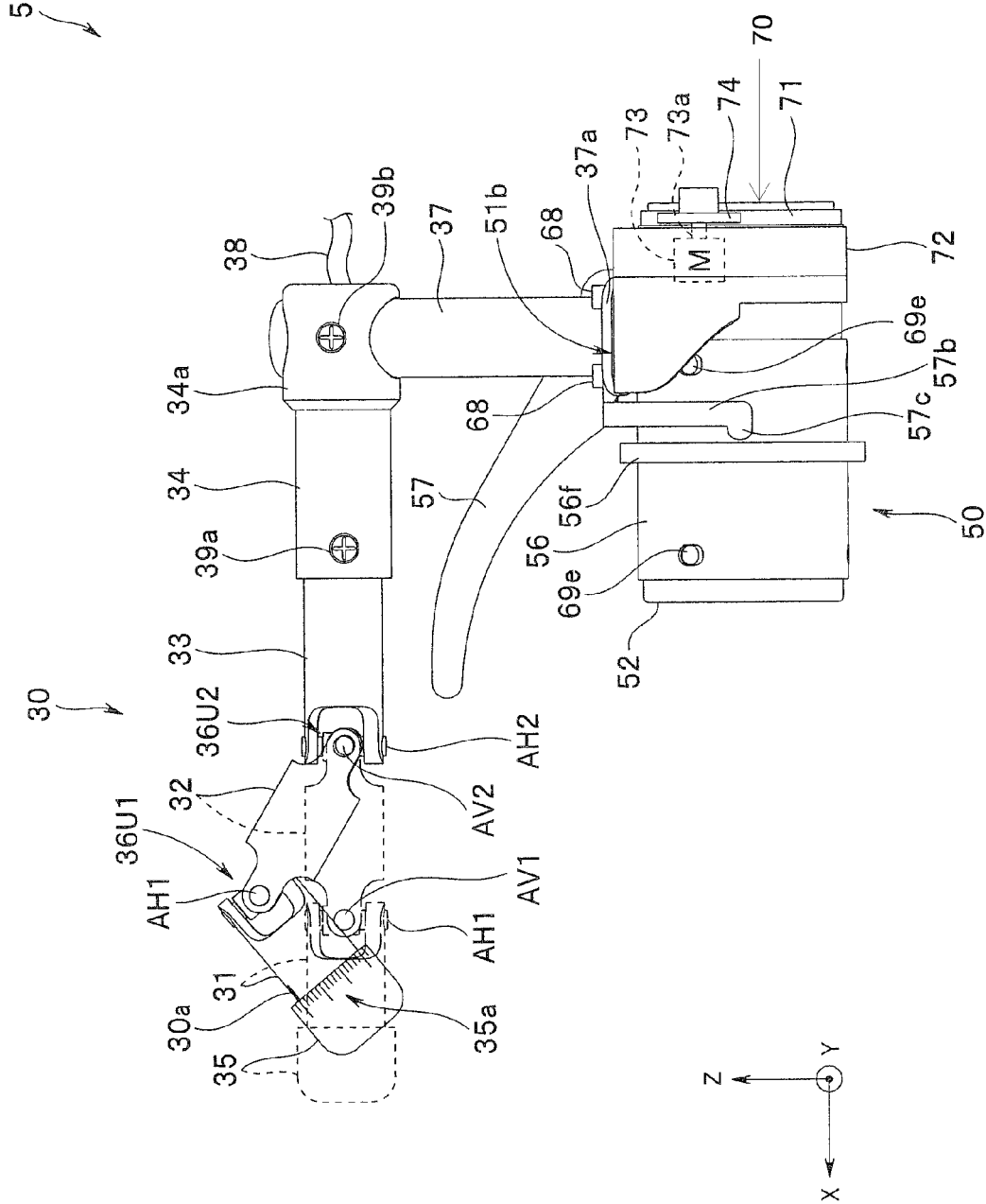
FIG. 3 is a left side view of the electric bending operation device in FIG. 2.
Figure 4:
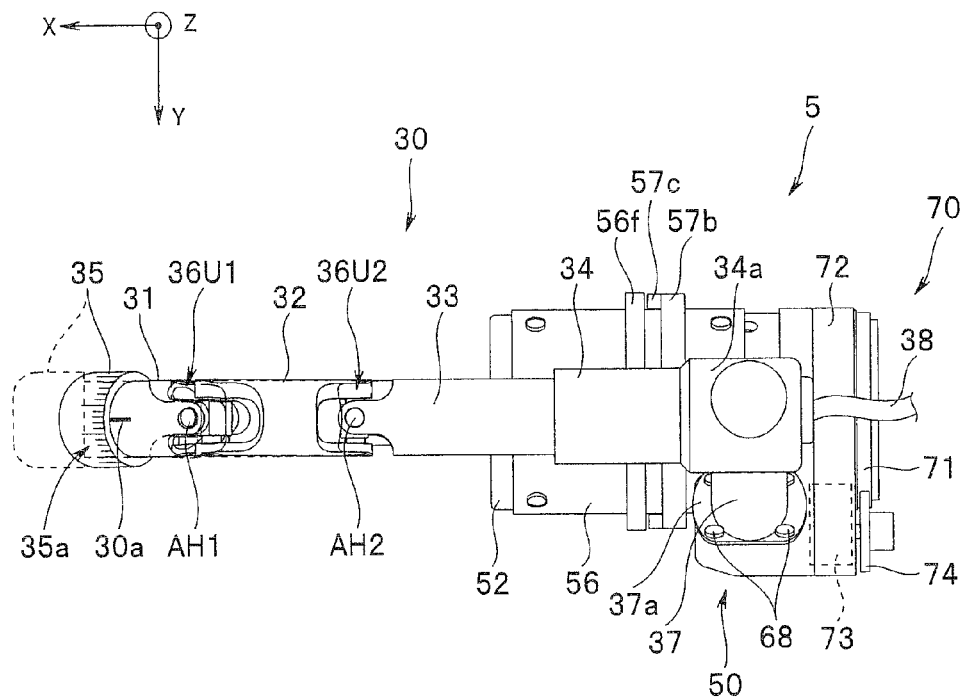
FIG. 4 is a top view of the electric bending operation device in FIG. 2.

With reference to FIGS. 2, 3 and 4, the insertion portion operation section 30 will be described.

In the present embodiment, the direction indicated by arrow X in FIGS. 2 to 4 is a distal end direction and the opposite direction is a proximal end direction, the direction indicated by arrow Y is a leftward direction and the opposite direction is a rightward direction, the direction indicated by arrow Z is an upward direction and the opposite direction is a downward direction.

As shown in FIGS. 2 to 4, the insertion portion operation section 30 includes a first rod 31, a second rod 32, and a twisting operation portion 35 of pipe shape. In the present embodiment, the insertion portion operation section 30 is mounted to an operation portion support member 34 via a fixing rod 33.

At a distal end portion of the first rod 31, the cylindrical twisting operation portion 35 is provided. The twisting operation portion 35 is placed rotatably relative to an outer peripheral surface of the distal end portion of the first rod 31. Specifically, the twisting operation portion 35 rotates around an axis of the first rod, an X-axis in the drawings.

The twisting operation portion 35 is a twisting detection encoder that detects the direction and the amount of rotation. The twisting operation portion 35 outputs a twisting control signal for indicating the direction and the amount of rotation to the twisting control portion 3b that is a second drive control portion of the endoscope control device 3 when rotated clockwise or counterclockwise seen from the side of the operation portion support member 34. Simultaneously with an input of the twisting control signal, the twisting control portion 3b calculates the amount of driving of an insertion portion rotation motor (reference numeral 73 in FIG. 3 described later) corresponding to the twisting control signal, and outputs a twisting operation signal to the insertion portion rotation motor. Then, the insertion portion 11 is twisted by a driving force of the insertion portion rotation motor so as to correspond to the operator's rotation operation of the twisting operation portion 35.

The first rod 31 is a first shape indication operation portion that serves as a first bending portion operation section and a first bending portion shape indication section that indicates a bending shape of the first bending portion. The first rod 31 is rotatably connected to a distal end portion of the second rod 32 via a universal joint 36U1. Specifically, the first rod 31 is rotatable around a first horizontal axis AH1 parallel to a Y-axis, and around a first vertical axis AV1 parallel to a Z-axis in the drawings.

The second rod 32 is a second shape indication operation portion that serves as a second bending portion operation section and a second bending portion shape indication section that indicates a bending shape of the second bending portion. The second rod 32 is rotatably connected to a distal end portion of the fixing rod 33 via a universal joint 36U2. Like the first rod 31, the second rod 32 is rotatable around a second horizontal axis AH2 parallel to the Y-axis, and around a second vertical axis AV2 parallel to the Z-axis in the drawings.

The universal joints 36U1 and 36U2 include a first bending detection portion and a second bending detection portion, respectively. The bending detection portions each include a potentiometer, or a noncontact magnetic sensor, an optical sensor, or the like, and detect the direction and the amount of rotation of the rods 31 and 32 with respect to the axes AH1 and AH2 and the direction and the amount of rotation of the rods 31 and 32 with respect to the vertical axes AV1 and AV2.

When the first rod 31 is rotated with respect to the first horizontal axis AH1 or the first vertical axis AV1, the first bending detection portion outputs a first rod rotation control signal for indicating the direction and the amount of rotation of the first rod 31 with respect to the axis AH1 or AV1 to the bending control portion 3a of the endoscope control device 3 similarly to the case where the first vertically bending knob 23UD or the first laterally bending knob 23RL is operated clockwise or counterclockwise.

On the other hand, when the second rod 32 is rotated with respect to the second horizontal axis AH2 or the second vertical axis AV2, the second bending detection portion outputs a second rod rotation control signal for indicating the direction and the amount of rotation of the second rod 32 with respect to the axis AH2 or AV2 to the bending control portion 3a of the endoscope control device 3 similarly to in the case where the second vertically bending knob 24UD or the second laterally bending knob 24RL is operated clockwise or counterclockwise.

Simultaneously with an input of the rod rotation control signal from the first bending detection portion or the second bending detection portion, the bending control portion 3a calculates the amount of pull of an angle wire by a wire drive motor corresponding to the rod rotation control signal, and outputs a bending control signal to the corresponding wire drive motor. Thus, the wire drive motor corresponding to the operator's rod operation is driven, causing bending operation of the electric bending portion 15 similarly to the case where the first bending portion operation section 21 and the second bending portion operation section 22 are operated. The fixing rod 33 is integrally secured to the distal end side of the operation portion support member 34, for example, by a screw 39a.

The operation portion support member 34 also serves as a grasping portion, and has a proximal end portion 34a integrally secured to a support column 37, for example, by a screw 39b. A longitudinal axis of the operation portion support member 34 and the X-axis of the electric bending operation device 5 are set in parallel with each other.

In the present embodiment, the operation portion support member 34 is secured to the support column 37. However, the fixing rod 33 and the operation portion support member 34 may be integrally formed to be secured to the support column 37, or the insertion portion operation section 30 may be mounted to the operation portion support member 34.

In the present embodiment, the first rod 31 and the second rod 32 including the universal joints include the potentiometers, and the potentiometers include friction resistance portions (not shown). The friction resistance portions are provided to prevent operating errors, and the first rod 31 and the second rod 32 are rotated when a rotating force higher than a preset force is applied.

The first rod 31 and the second rod 32 have the friction resistance portions, and thus when rotation operation is stopped, the first rod 31 and the second rod 32 are maintained with the rotation operation being stopped by frictional forces of the friction resistance portions. Specifically, the first rod 31 shows the bending shape of the first bending portion 17 of the electric bending portion 15, and the second rod 32 shows the bending shape of the second bending portion 18 of the electric bending portion 15.

Thus, the operator can visually check the vertical and lateral tilt of the first rod 31 and the vertical and lateral tilt of the second rod with reference to the fixing rod 33, and thus can easily perceive a general bending state of the electric bending portion 15. Specifically, the first rod 31 and the second rod 32 are bending portion operation sections that operate the bending portions 17 and 18, and also bending portion shape indication sections that indicate the bending shapes of the bending portions 17 and 18.

The twisting operation portion 35 may be a graduation ring having graduations 35a circumferentially provided at an outer edge of a proximal end of the twisting operation portion 35, for visual check of the amount of twisting operation instruction. With the configuration, before the start of endoscopy, a zero point on the graduation ring is aligned with a reference line 30a. Thus, the graduations 35a can be checked to check the amount of twisting of the insertion portion 11 after the rotation operation of the twisting operation portion 35. Specifically, the twisting operation portion 35 having the graduations 35a is an insertion portion twisting amount indication section that indicates the amount of twisting of the insertion portion 11.

In the present embodiment, the frictional forces of the friction resistance portions are set to be larger in the order of the twisting operation portion 35, the first rod 31, and the second rod 32 so that the twisting operation portion 35 is rotated most easily. This prevents the first rod 31 from vertically rotating, for example, when the twisting operation portion 35 is operated with the first bending portion 17 laterally bending. This also prevents the second rod 32 from rotating when the first rod 31 is operated with the second bending portion 18 bending.

In the present embodiment, the general bending state of the electric bending portion 15 can be perceived from the tilts of the rods 31 and 32. This is because, for example, an upward bending angle of the first bending portion 17 is 210 degrees, while an upward angle of the rod 31 is set to be smaller than the degree by a predetermined angle for operability of the first rod and the second rod. Specifically, the amounts of bending of the first rod and the second rod and the amounts of bending of the first bending portion and the second bending portion are not similar.

Signal wires extending from the twisting operation portion 35, the first bending detection portion, and the second bending detection portion are passed through a protective tube 38 extending from the proximal end portion 34a of the operation portion support member 34 and connected to the endoscope control device 3.

Next, with reference to FIGS. 2 to 7, the insertion portion mounting mechanism 50 including the rotation mechanism 70 will be described.

First, the insertion portion mounting mechanism 50 will be described.

As shown in FIGS. 2 to 6, the insertion portion mounting mechanism 50 mainly includes a rotation holding portion 51, a rotary cylinder 52 that also serves as the rotation mechanism 70, a plurality of pawl members 53 that are insertion portion pressing members, a pair of switching cylinders 54a and 54b, a biasing member 55, a movable cylinder 56, and a lever 57. Reference numerals 58a and 58b denote lids. The lids 58a and 58b are secured to a distal end surface and a proximal end surface, respectively, of the rotary cylinder 52.

Figure 5:
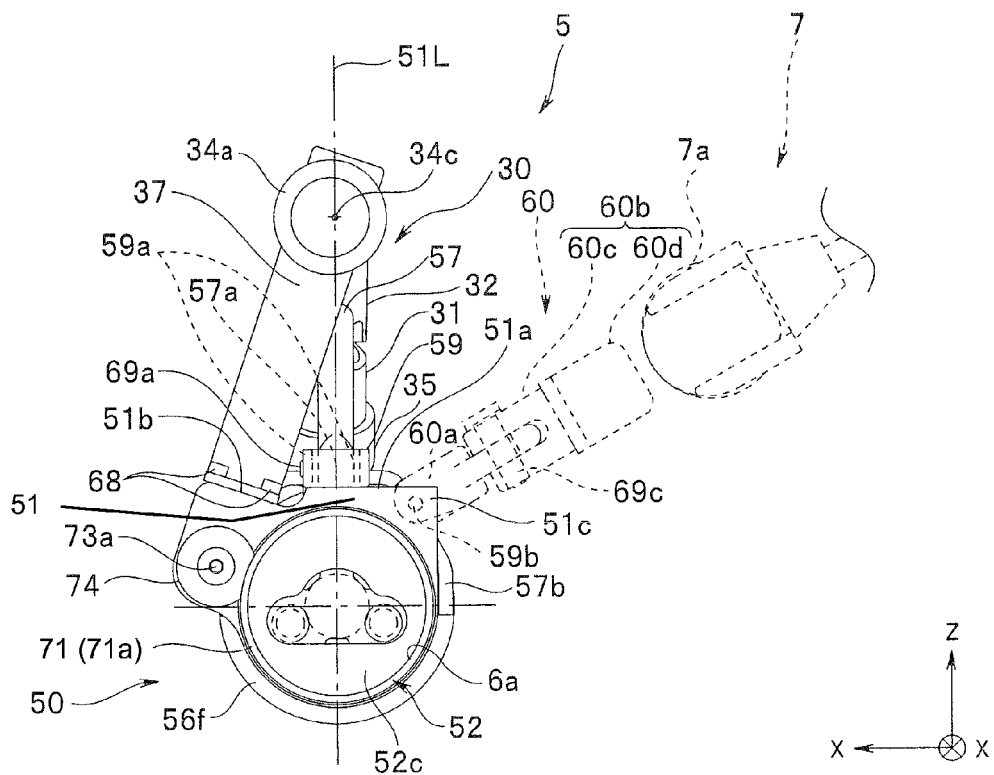
FIG. 5 is a back view of a proximal end surface of the electric bending operation device in FIG. 2.
Figure 6:
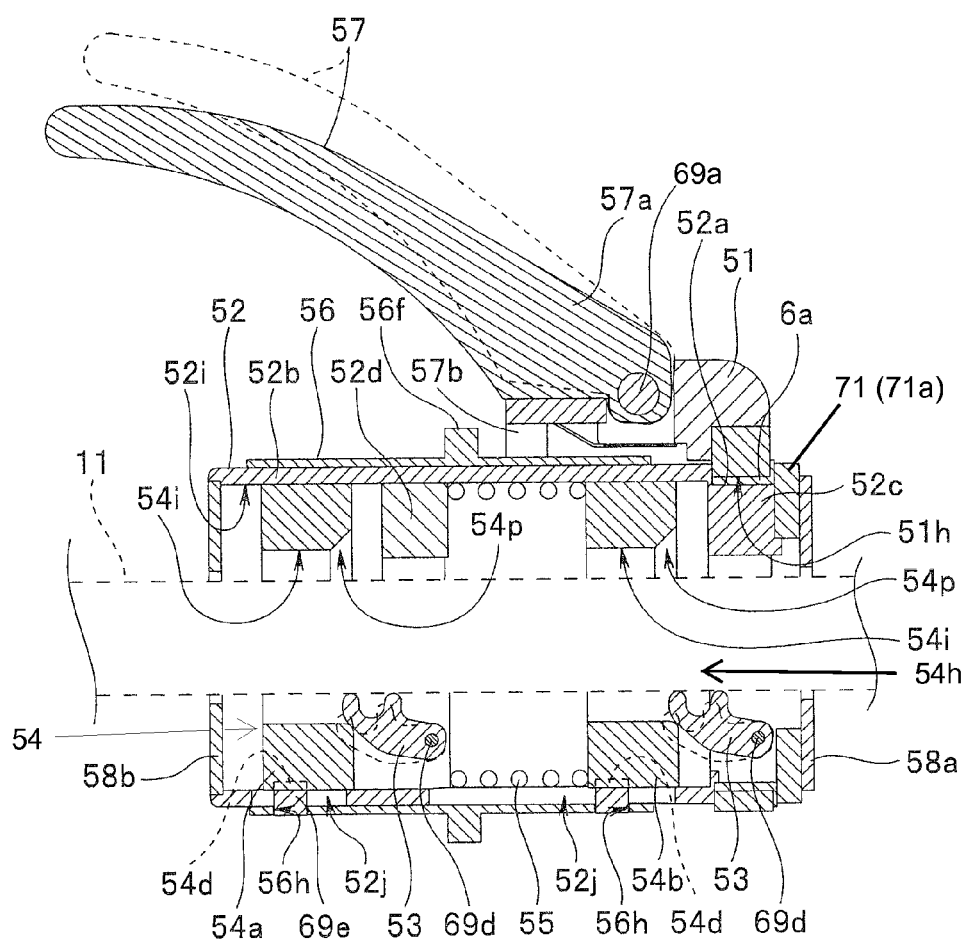
FIG. 6 is a sectional view for illustrating a configuration of an insertion portion mounting mechanism.

The rotation holding portion 51 is a device body and has a through hole 51h, in which a bearing 6a is provided, as shown in FIGS. 5 and 6. On the bearing 6a, the rotary cylinder 52 is rotatably placed.

As shown in FIG. 5, in the rotation holding portion 51, a support column mounting portion 51b and a securing arm attaching/detaching portion 51c are provided with a lever mounting portion 51a therebetween.

To the lever mounting portion 51a, a lever support member 59 is threadedly secured. As shown in FIGS. 5 and 6, the lever support member 59 includes a pair of standing support portions 59a, and between the support portions 59a, a fulcrum 57a of the lever 57 is placed. The fulcrum 57a is provided on a centerline 51L extending in parallel with the Z-axis from the center of the through hole 51h.

The fulcrum 57a is rotatably mounted to the support portion 59a by a first pin 69a. Thus, the lever 57 is a switching mechanism, and moves from the position shown by the solid line to the position shown by the broken line in FIG. 6.

As shown in FIGS. 2 to 5, an inverted U-shaped arm 57b is integrally secured to the lever 57. The arm 57b has pressing portions 57c at opposite ends. When the lever 57 is moved in the direction shown by the broken line in FIG. 6, the pressing portions 57c abut against a side surface on a proximal end side of an outer flange 56f provided on the movable cylinder 56 to move the movable cylinder 56 relative to the rotary cylinder 52.

To the support column mounting portion 51b, the support column 37 is mounted. The support column 37 has a flange 37a on one end, and is integrally secured by a plurality of screws 68 with the flange 37a placed on the support column mounting portion 51b.

The center 34c of the proximal end portion 34a provided at the end of the support column 37 standing on the support column mounting portion 51b is provided on the centerline 51L extending from the center of the through hole 51h. Specifically, the operation portion support member 34 and the lever 57 are placed in one plane including the centerline 51L. The center of gravity of the electric bending operation device 5 is adjusted so as to be placed in the plane. Thus, the −Z direction of the centerline 51L is the direction of the center of gravity of the electric bending operation device 5, and an operation direction of the lever 57 matches the direction of the center of gravity of the electric bending operation device 5. Thus, the lever 57 can be operated by fingers with a palm placed on the operation portion support member 34, thereby allowing efficient lever operation without rotation moment caused by gravity.

In the securing arm attaching/detaching portion 51c, an arm mounting member 60 is provided having a mounting tool 60d detachably attached to an attaching/detaching portion 7a of the securing arm 7 as shown by the broken line in FIG. 5. The arm mounting member 60 includes a rotation holding portion mounting section 60a and a securing arm mounting portion 60b.

One end of the rotation holding portion mounting section 60a holds the securing arm attaching/detaching portion 51c and is rotatably mounted by a second pin 69b. Thus, the rotation holding portion mounting section 60a is provided so as to protrude outward from a peripheral surface of the rotation holding portion 51. To the other end of the rotation holding portion mounting section 60a, a connecting portion 60c that forms one end of the securing arm mounting portion 60b is rotatably mounted by a third pin 69c.

At the other end of the securing arm mounting portion 60b, the mounting tool 60d is provided, which is rotatable around the second pin and the third pin. The mounting tool 60d is integrally secured to the attaching/detaching portion 7a of the securing arm 7 by locking.

As shown in FIG. 6, the rotary cylinder 52 includes a rotating portion 52a and a sliding portion 52b on an outer peripheral surface thereof. The rotating portion 52a is rotatably held by the bearing 6a provided in the rotation holding portion 51. On an outer periphery of the sliding portion 52b, the movable cylinder 56 that constitutes the switching mechanism is slidably placed.

The rotary cylinder 52 has protrusions 52c and 52d protruding toward a central axis on a proximal end side and a middle portion of an inner peripheral surface. In the present embodiment, the protrusion 52c is formed on the rotary cylinder 52. On the other hand, the protrusion 52d is integrally secured to the inner peripheral surface of the rotary cylinder 52, for example, from the side of the outer peripheral surface by threading or bonding, and is provided on the rotary cylinder 52.

Now, with reference to FIG. 7, the protrusion 52*d* will be described. The configuration of the protrusion 52*c* is substantially the same as that of the protrusion 52*d*, and thus the configuration of the protrusion 52*d* will be described and the description on the protrusion 52*c* will be omitted.

Figure 7:
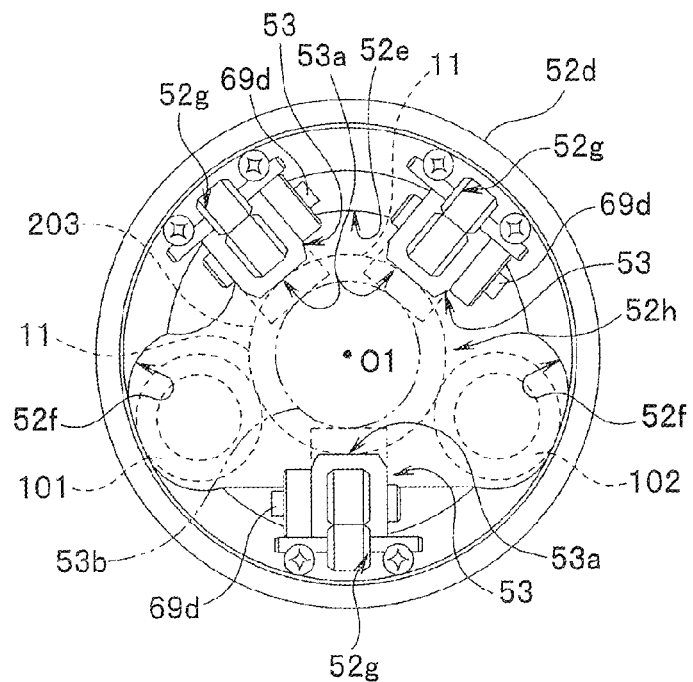
FIG. 7 illustrates a configuration of an insertion portion pressing member and a relationship between the insertion portion pressing member and an insertion portion.

The protrusion 52*d* shown in FIG. 7 provided on the distal end side has a through hole 52*h* through which the insertion portion 11 shown by the broken line and a pair of external tubes (reference numerals 101 and 102 in FIG. 9) shown by the broken lines and described later pass. The through hole 52*h* includes an insertion portion passing hole 52*e* through which the insertion portion 11 pass, and a pair of tube passing holes 52*f* through which the external tubes 101 and 102 pass.

The protrusion 52*d* has three notch recesses 52*g* in which the pawl members 53 that are insertion portion pressing members are placed. The three notch recesses 52*g* are provided radially from the center O1. The pawl member 53 placed in each notch recess 52*g* is mounted so as to rotate a pin 69*d* toward the center O1. Reference numeral 53*a* denotes a pressing portion, which presses and securely holds an outer surface of the insertion portion 11 shown by the broken line. Placement positions of the pawl members 53 are set so that a longitudinal axis of the insertion portion 11 is placed on the center O1 when the insertion portion 11 is securely held by the three pressing portions 53*a*.

When the pawl members 53 are moved closest to the center O1 as shown by the dash-double-dot line, an imaginary circle 53*b* inscribed in the three pressing portions 53*a* and shown by the dash-double-dot line has a diameter smaller than an outer diameter of the insertion portion 11 by a predetermined amount.

With the lever being grasped, each pressing portion 53*a* is placed in a retraction position where no pressing force is applied to the insertion portion 11 as shown by the broken line in FIG. 6 and the solid line in FIG. 7, by a biasing force of an unshown spring provided in the pawl member 53. While the pressing portion 53*a* is moved to the retraction position, the electric bending operation device 5 can be advanced or retracted with respect to the insertion portion 11.

As shown in FIG. 6, the switching cylinders 54 that constitute the switching mechanism are placed slidably with respect to an inner peripheral surface 52*i*, between the protrusion 52*c* and the protrusion 52*d* provided on the rotary cylinder 52 and on the other end side of the protrusion 52*d*, on the side of the inner peripheral surface 52*i* of the rotary cylinder 52.

Figure 8:
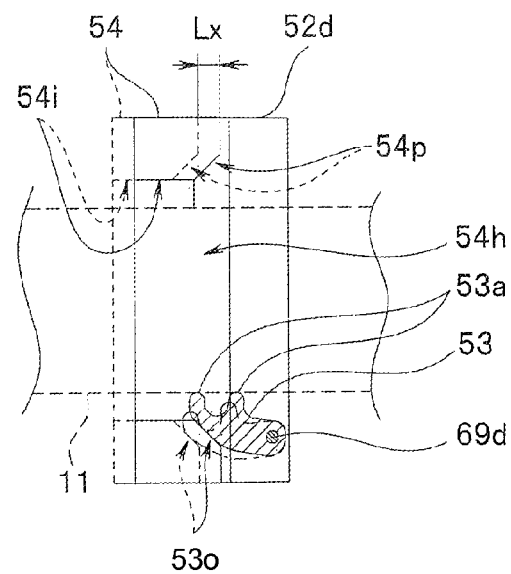
FIG. 8 illustrates operation of a switching cylinder and operation of the insertion portion pressing member.

Each switching cylinder 54 is cylindrical, and has an axial press hole 54*h* that provides communication between an inner space 54*i* and the outside as shown in FIG. 8. An inner surface of the press hole 54*h* is formed as a press surface 54*p*. The press surface 54*p* is tapered with a decreasing inner diameter from an opening toward the inner space 54*i*.

In the press hole 54*h*, the pawl member 53 rotatably placed in each of the protrusions 52*c* and 52*d* is placed. When the pawl member 53 is placed in the press hole 54*h*, the press surface 54*p* abuts against an outer side surface 53*o* of the pawl member 53 as shown by the broken line. When the switching cylinder 54 is moved, in the abutting state, from the position shown by the broken line, for example, by a distance Lx by the biasing member 55 as shown by the solid line, the press surface 54*p* presses the outer side surface 53*o* of the pawl member 53 with the movement of the switching cylinder 54. Then, the pressing portion 53*a* presses the outer surface of the insertion portion 11 shown by the broken line.

As shown in FIG. 6, the switching cylinder 54 has a pin hole 54*d* in an outer peripheral surface thereof. In the pin hole 54*d*, a slide pin 69*e* is integrally secured by swaging or threading. The slide pin 69*e* has a length protruding outward from the outer peripheral surface of the sliding portion 52*b* through a slot 52*j* formed in the sliding portion 52*b* of the rotary cylinder 52. The slot 52*j* is a through hole that provides communication between the inner peripheral surface and the outer peripheral surface of the rotary cylinder 52, and formed in parallel with the longitudinal axis of the rotary cylinder 52.

The movable cylinder 56 is slidably provided on the sliding portion 52*b* of the rotary cylinder 52. The movable cylinder 56 has an outer flange 56*f* at a predetermined position in the middle portion of the outer peripheral surface. The pressing portions 57*c* of the arm 57*b* abut against the outer flange 56*f*. When the lever 57 is moved in the direction shown by the broken line in FIG. 6, the movable cylinder 56 is moved toward the distal end. The movable cylinder 56 has two pin holes 56*h* in which the slide pins 69*e* are placed. The pin hole 56*h* is a through hole that provides communication between the inner surface and the outer surface of the movable cylinder 56.

The biasing member 55 is a compression coil spring. The biasing member 55 is placed between the protrusion 52*d* and the switching cylinder 54 on the side of the protrusion 52*c*. Among the pair of switching cylinders 54, one provided on the side of the protrusion 52*d* is a first switching cylinder 54*a*, and one provided on the side of the protrusion 52*c* is a second switching cylinder 54*b* for description.

The biasing member 55 has a biasing force for moving the two switching cylinders 54*a* and 54*b* toward the proximal end to press the insertion portion 11 with the pressing portions 53*a* of the pawl members 53 and integrally holding the insertion portion 11. The two switching cylinders 54*a* and 54*b* are integrally moved toward the proximal end as shown in FIG. 8 by the second switching cylinder 54*b* being moved by the biasing force of the biasing member 55.

Now, the configuration in which the two switching cylinders 54*a* and 54*b* are integrally moved will be described.

An assembly operator previously provides the second switching cylinder 54*b*, the biasing member 55, the protrusion 52*d*, and the first switching cylinder 54*a* on the inner peripheral surface of the rotary cylinder 52. Then, the operator places the movable cylinder 56 on the sliding portion 52*b* of the rotary cylinder 52.

Then, the operator places the slide pins 69*e* in the pin holes 54*d* in the switching cylinders 54*a* and 54*b* through the pin holes 56*h* in the movable cylinder 56 and the slots 52*j*. Then, the operator secures the slide pins 69*e* in the switching cylinders 54*a* and 54*b* by threading or swaging. Thus, the two switching cylinders 54*a* and 54*b* are placed slidably with respect to the inner peripheral surface of the rotary cylinder 52, and the movable cylinder 56 is placed slidably with respect to the sliding portion 52*b* of the rotary cylinder 52. The movable cylinder 56 and the two switching cylinders 54 integrally slide with respect to the rotary cylinder 52.

Thus, when the second switching cylinder 54*b* is moved toward the protrusion 52*c* by the biasing force of the biasing member 55, the movable cylinder 56 and the first switching cylinder 54*a* are integrally moved toward the proximal end with the movement of the second switching cylinder 54*b*. Then, the press surfaces 54*p* of the switching cylinders 54*a* and 54*b* move the pawl members 53 rotatably provided in the protrusion 52*d* toward the center O1 of the insertion portion passing hole 52*e*.

On the other hand, when the lever 57 is moved in the direction shown by the broken line in FIG. 6 to move the movable cylinder 56 toward the distal end, the switching cylinders 54*a* and 54*b* are moved toward the distal end against the biasing force of the biasing member 55 with the movement of the movable cylinder 56. Then, the press surfaces 54p of the switching cylinders 54a and 54b cause the pawl members 53 having been moved toward the center O1 of the insertion portion passing hole 52e to be moved apart from the center O1.

Finally, the rotation mechanism 70 provided in the insertion portion mounting mechanism 50 will be described.

As shown in FIGS. 3 and 4, the rotation mechanism 70 mainly includes a cylinder gear 71 provided on the rotary cylinder 52, and an insertion portion rotation motor 73 provided in a motor housing 72 integrally secured to the rotation holding portion 51. The insertion portion rotation motor 73 generates a driving force for rotating the rotary cylinder 52.

As shown in FIG. 5, the cylinder gear 71 is provided on an outer periphery of the rotating portion 52a of the rotary cylinder 52 protruding from the through hole 51h in the rotation holding portion 51. The cylinder gear 71 is a cylinder side spur gear 71a having a tooth trace formed in parallel with the central axis of the rotary cylinder 52. To a motor shaft 73a of the insertion portion rotation motor 73, a motor side spur gear 74 that meshes with the cylinder side spur gear 71a is secured.

With the configuration, a rotation driving force of the insertion portion rotation motor 73 is transmitted to the cylinder side spur gear 71a via the motor shaft 73a and the motor side spur gear 74, causing the rotary cylinder 52 to rotate relative to the rotation holding portion 51. At this time, the movable cylinder 56, the protrusions 52d, and the switching cylinders 54a and 54b integrally rotate with the rotation of the rotary cylinder 52. If the pressing portions 53a of the pawl members 53 provided in the protrusions 52c and 52d press the insertion portion 11, the insertion portion 11 also rotates with the rotary cylinder 52.

Operations of the endoscope system 1 including the electric bending operation device 5 thus configured will be described.

Figure 9:
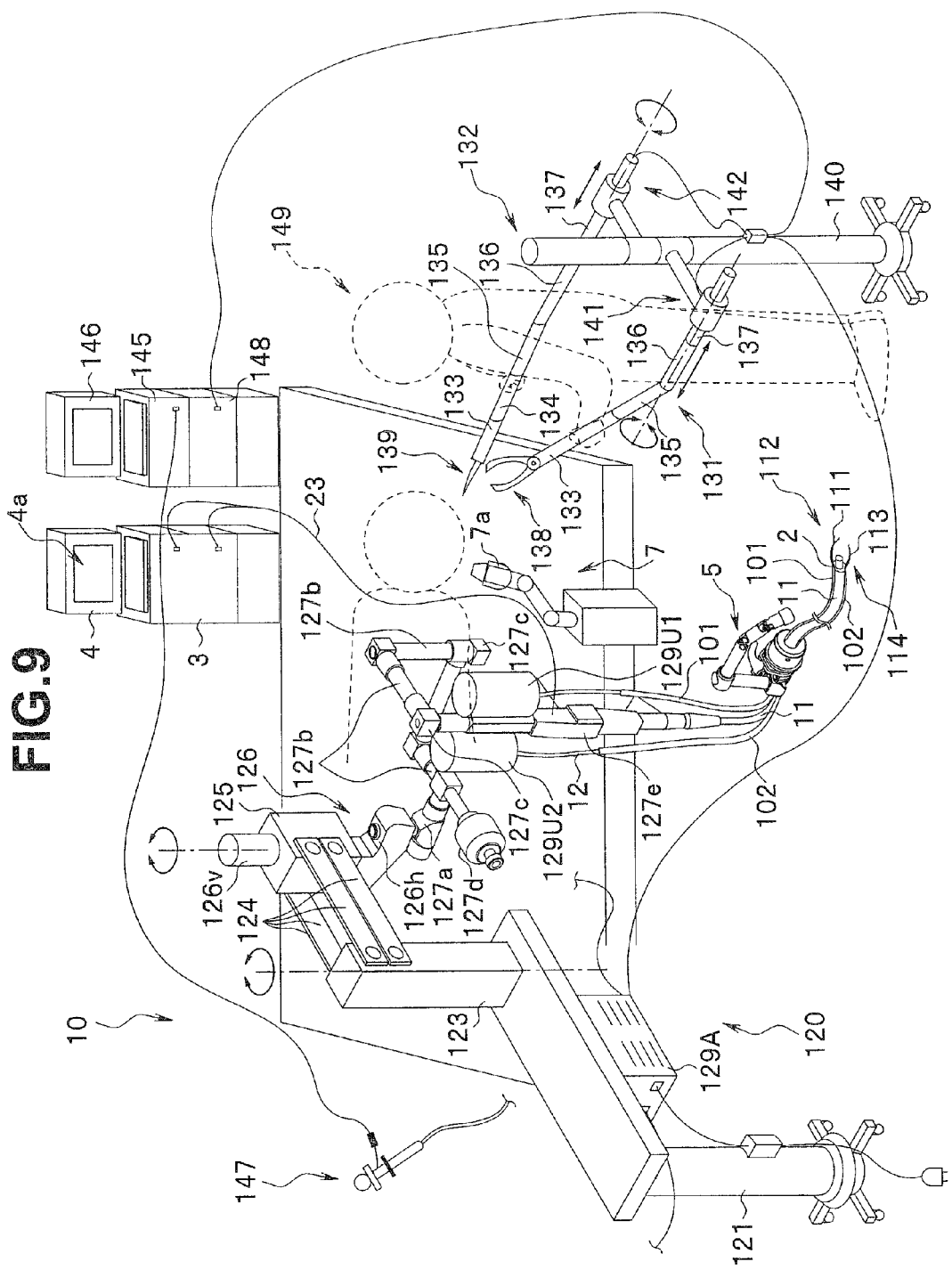
FIG. 9 illustrates a medical system including an endoscope system.

The endoscope system 1 in the present embodiment is configured, for example, as a medical treatment system 10 in FIG. 9. The medical treatment system 10 includes, besides the endoscope system 1, for example, the pair of external tubes 101 and 102, a plurality of manipulator devices 110, a support base 120 including a scope holder, a manipulator operation device 130, or the like.

The plurality of manipulator devices 110 include, for example, a grasping manipulator 112 including a hand arm 111, and a high frequency manipulator 114 including a knife arm 113. The positions and the attitudes of the hand arm 111 and the knife arm 113 of the manipulator devices 110 are set by operating master portions 131 and 132 provided in the manipulator operation device 130.

The manipulator operation device 130 includes a grasping tool master portion 131 and a high frequency master portion 132. The master portions 131 and 132 are input devices for setting angles or axial positions of a plurality of unshown joints provided in the grasping manipulator 112 and the high frequency manipulator 114. The master portions 131 and 132 are slidably mounted to holding portions 141 and 142 provided on a stand 140.

Each of the master portions 131 and 132 includes master side joint pieces 133, 134, 135, 136 and 137 corresponding to the plurality of joints of the manipulators 112 and 114, a master side hand arm 138, and a master side knife arm 139.

Insertion portions provided in the grasping manipulator 112 and the high frequency manipulator 114 are passed through the pair of external tubes 101 and 102 provided along the insertion portion 11 of the electric bending endoscope 2. In the drawing, the grasping manipulator 112 is passed through the first external tube 101, and the grasping manipulator 112 is passed through the second external tube 102.

The support base 120 includes a support column 121. A table 122 is secured on the support column 121. A vertical arm 123 stands on an upper surface of the table 122. The vertical arm 123 is rotatably mounted to the table 122. On the vertical arm 123, a first arm holding member 125 is provided, for example, via a plurality of securing members 124. To the first arm holding member 125, a vertical arm portion 126v of an L-shaped arm 126 is rotatably mounted. To a horizontal arm portion 126h of the L-shaped arm 126, a scope holder for manipulator (hereinafter referred to as a scope holder) 127 is mounted. The scope holder 127 includes a rotation support portion 127a, a plurality of arms 127b, a rotational joint 127c, a weight 127d, and a securing portion 127e. The operation portion 12 of the electric bending endoscope 2 mounted to the securing portion 127e can be freely changed in the direction and the attitude.

Reference numerals 129U1 and 129U2 denote manipulator drive units, which are mounted to the securing portion 127e. In the manipulator drive units 129U1 and 129U2, a plurality of arm drive motors (not shown) that pull and loosen a plurality of angle wires for operating the joints of the manipulators 112 and 114, or manipulator drive motors that advance or retract the manipulator devices 110 are provided.

Reference numeral 129A denotes a manipulator control box, in which a control circuit (not shown) is provided that controls the plurality of arm drive motors or the like provided in the manipulator drive units 129U1 and 129U2. The manipulator control box 129A is electrically connected to the manipulator operation device 130 and a control device 145 via signal cables.

Reference numeral 146 denotes a manipulator side monitor. Reference numeral 147 denotes a high frequency manipulator handlebar. The high frequency manipulator handlebar 147 is connected to a high frequency power supply device 148 via an electric cable, and supplies high frequency power. Reference numeral 149 denotes an operator.

Figure 10:
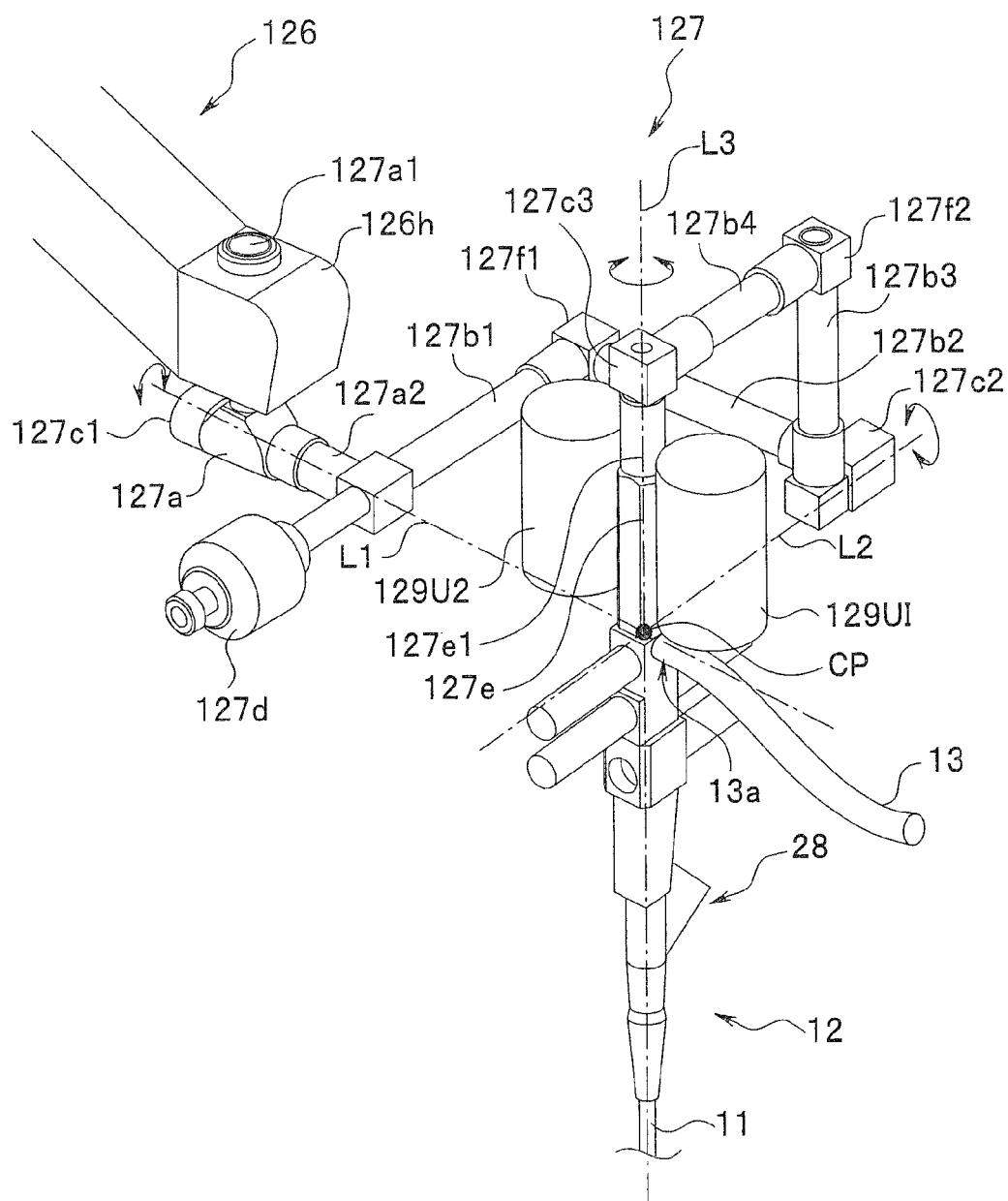
FIG. 10 illustrates an exemplary configuration of a scope holder.

With reference to FIG. 10, a configuration of the scope holder 127 will be described in detail.

The scope holder 127 includes the rotation support portion 127a including a first rotational joint 127c1, a first arm 127b1, a second arm 127b2, a third arm 127b3, a fourth arm 127b4, a second rotational joint 127c2, a third rotational joint 127c3, the weight 127d, the securing portion 127e, and a plurality of connectors 127f. The weight 127d is a so-called a counterweight for countering the moment of inertia, and provided at an end of the first arm 127b1.

The rotation support portion 127a that constitutes the scope holder 127 is rotatably mounted to a horizontal arm portion 126h via a rotating shaft 127a1. To the rotation support portion 127a, the first arm 127b1 is rotatably mounted at a rotation holding portion 127a2.

The first arm 127b1 and the second arm 127b2 are connected via a first connector 127f1. The second arm 127b2 and the third arm 127b3 are rotatably mounted via the second rotational joint 127c2. The third arm 127b3 and the fourth arm 127b4 are connected via a second connector 127f2. To the fourth arm 127b4, a securing portion 127e1 in the securing portion 127e is rotatably mounted via the third rotational joint 127c3.

In the present embodiment, a first rotating shaft extension line L1 of the first rotational joint provided in the rotation support portion 127a, a second rotating shaft extension line L2 of the second rotational joint 127c2, and a third rotating shaft extension line L3 of the third rotational joint 127c3 cross substantially at one point, a crosspoint CP. The first rotating shaft extension line L1, the second rotating shaft extension line L2, and the third rotating shaft extension line L3 are formed as imaginary X-, Y-, and Z-axes.

The securing portion 127e1 can be replaced by one having a different length so that the extending portion 13a of the universal cord 13 extending from the side of the operation portion 12 secured to the securing portion 127e extends from the crosspoint CP or from in the vicinity of the crosspoint CP.

The universal cord 13 of the electric bending endoscope 2 extends from the crosspoint CP to eliminate rotation moment (F×Lz) generated by the extending portion 13a being spaced apart from the crosspoint CP, for example, by a distance Lz. This improves operator's operability in inserting the insertion portion 11 while grasping the electric bending operation device 5 as described later.

When the extending portion 13a is spaced apart from the crosspoint CP by the distance Lz, generation of the rotation moment (F×Lz) may be eliminated by securing the distal end side from the extending portion 13a of the universal cord 13 in the vicinity of the crosspoint CP.

Operations of the medical treatment system 10 will be described.

In use of the medical treatment system 10, a user mounts the external tubes 101 and 102 to the insertion portion 11 of the electric bending endoscope 2. The user also mounts the operation portion 12 of the electric bending endoscope 2, to which the external tubes 101 and 102 are mounted, to the securing portion 127e of the scope holder 127. Then, the electric bending operation device 5 is placed in the flexible tube 16 of the insertion portion 11.

At this time, the user moves the lever 57 from the position shown by the solid line to the position shown by the broken line in FIG. 6 to hold the lever 57 in the position shown by the broken line. Thus, the pressing portions 53a of the pawl members 53 provided in the rotary cylinder 52 of the electric bending operation device 5 are moved to the retraction position.

Then, the user passes the insertion portion 11, to which the external tubes 101 and 102 are mounted, through the through hole 52h from the proximal end side of the electric bending operation device 5. At this time, since the through hole 52h has the insertion portion passing hole 52e and the pair of tube passing holes 52f, the insertion portion 11 to which the external tubes 101 and 102 are mounted is passed through the through hole 52h in a predetermined direction.

Then, when the electric bending operation device 5 reaches a predetermined position in the flexible tube 16, the user releases the holding state of the lever 57. Then, the two switching cylinders 54a and 54b are moved toward the proximal end by the biasing force of the biasing member 55, the pressing portions 53a of the pawl members 53 press the flexible tube 16, and the electric bending operation device 5 is integrally provided in the flexible tube 16.

The operator 149 passes the insertion portion 11, to which the external tubes 101 and 102 are mounted, into the body while, for example, observing endoscopic images displayed on the screen 4a of the display device 4. At this time, since the operation portion 12 is held in the securing portion 127e of the scope holder 127, the operator grasps, for example, the operation portion support member 34 of the electric bending operation device 5 by one hand, and holds the insertion portion 11 by the other hand.

Then, the operator 149 performs operations of moving the lever 57 of the electric bending operation device 5 to the position shown by the solid line and the position shown by the broken line in FIG. 6, rotating the first rod 31 and the second rod 32 of the insertion portion operation section 30, and rotating the twisting operation portion 35, and thus passes the insertion portion 11 into a deep part in the body so that a target observation region is displayed on the screen 4a.

Then, to start insertion of the treatment instrument or treatment with the manipulators 112 and 114, the operator rotates the mounting tool 60d of the securing arm mounting portion 60b around the second pin or the third pin so as to be aligned with the attaching/detaching portion 7a of the securing arm 7, and then integrally secures the mounting tool 60d to the attaching/detaching portion 7a. Thus, the electric bending operation device 5 is supported by the securing arm 7. This allows the operator to take both hands off the electric bending endoscope 2.

Since the mounting tool 60d of the arm mounting member 60 protrudes outward from the peripheral surface, and can rotate around the second pin or the third pin, a mounting operation direction in mounting the mounting tool 60d to the attaching/detaching portion 7a can be easily set in a direction having the least effect on an insertion depth of the distal end portion or direction changes. Thus, when the mounting operation is completed, endoscopic images of the target observation region substantially similar to those displayed before mounting are displayed on the screen 4a.

Specifically, the operator 149 moves the electric bending operation device 5 while taking the hand off the lever 57 of the electric bending operation device 5 and grasping the operation portion support member 34. Then, with the movement of the electric bending operation device 5, the insertion portion 11 integrally secured to the electric bending operation device 5 is inserted into the patient's body. Then, the operator operates the lever 57 and the insertion portion operation section 30 as appropriate to insert the insertion portion 11 into the deep region in the body.

Specifically, the operator 149 repeatedly performs operations of inserting the insertion portion 11 into the body while taking the hand off the lever 57, moving the placement position of the electric bending operation device 5 with respect to the insertion portion 11 toward the proximal end while grasping the lever 57, and again inserting the insertion portion 11 into the body while taking the hand off the lever 57, thereby inserting the insertion portion 11 into the body.

When inserting the insertion portion 11 into the body while taking the hand off the lever 57, the operator 149 operates the first rod 31, the second rod 32, or the twisting operation portion 35. When the operator 149 operates the rods 31 and 32, the first bending portion 17 and the second bending portion 18 of the electric bending portion 15 bend according to the operations of the first rod 31 and the second rod 32.

When the operator operates the twisting operation portion 35, the insertion portion 11 integrally secured to the pressing portion 53a of the pawl member 53 provided in the rotary cylinder 52 is rotated. When the insertion portion 11 is rotated, the rotary cylinder 52 rotates relative to the rotation holding portion 51. The operation portion support member 34 grasped by the operator 149 is secured to the rotation holding portion 51 via the support column 37.

Thus, according to the electric bending operation device 5 of the present embodiment, when the twisting operation portion 35 is operated to twist the insertion portion 11, the position of the insertion portion operation section 30 including the first rod 31, the second rod 32, and the twisting operation portion 35 does not change. Thus, the operator 149 can properly perceive the bending direction of the electric bending portion 15, that is, the operation directions of the first rod 31 and the second rod 32, and performs the bending operation of the first bending portion 17 and the second bending portion 18 of the electric bending portion 15.

In the present embodiment, the bending operation of the first bending portion 17 that constitutes the electric bending portion 15 is performed by the first rod 31, and the bending operation of the second bending portion 18 is performed by the second rod 32. Then, the states of the bending operation performed by the first rod 31 and the bending operation performed by the second rod 32 are maintained. Thus, the bending state of the first bending portion 17 and the bending state of the second bending portion 18 can be checked by visually checking the bending operation state of the first rod 31 and the bending operation state of the second rod 32.

Thus, with the distal end portion 14 of the electric bending endoscope 2 facing a region to be treated, the operator visually checks the bending operation states of the rods 31 and 32, and determines, for example, whether the bending states of the bending portions 17 and 18 are suitable for passing the treatment instrument.

When determining that the bending states are suitable, the operator starts the insertion of the treatment instrument or the treatment with the manipulators 112 and 114. On the other hand, when determining that the bending states are not suitable, the operator re-operates the rods 31 and 32 so as to become bending operation states suitable for passing the treatment instrument, causing the distal end portion 14 to again face the region to be treated, and shifting to the insertion of the treatment instrument, or the like.

In the present embodiment, the lever 57, the operation portion support member 34, and the center of gravity of the electric bending operation device 5 are placed in one plane, and the operation direction of the lever 57 matches the direction of the center of gravity of the electric bending operation device 5. Thus, rotation moment caused by gravity around the lever during the operation of the lever 57 is minimized. In the bending operation and the twisting operation of the insertion portion, rotation moment caused by gravity around the operation portion support member is minimized.

Thus, the electric bending operation device 5 can be always stably held. This allows reliable and proper operations of the rods 31 and 32 and the lever 57 of the electric bending operation device 5. This also allows smooth mounting of the electric bending operation device 5 to the arm mounting member 60.

Thus, according to the electric bending operation device, besides the bending operation of the electric bending portion, the twisting operation of the insertion portion can be performed without interfering with the bending operation of the electric bending portion. Also, the operation states of the rods for bending the electric bending portions provided in the electric bending operation device can be checked to perceive the bending states of the electric bending portions.

In the above described endoscope system 1, the electric bending operation device 5 includes the first rod 31 and the second rod 32. This is because the electric bending portion 15 includes the first bending portion 17 and the second bending portion 18. Thus, a configuration in which the electric bending portion 15 includes only the first bending portion 17, a configuration in which the second bending portion 18 bends only vertically, or a configuration in which a third bending portion that bends vertically and lateral or bends vertically is provided can be accommodated by mounting, to the fixing rod 33, rods 31 and 32 and a twisting operation portion 35 corresponding to the configuration of the bending portion of the electric bending portion 15, or rods having other configurations.

Figure 11:
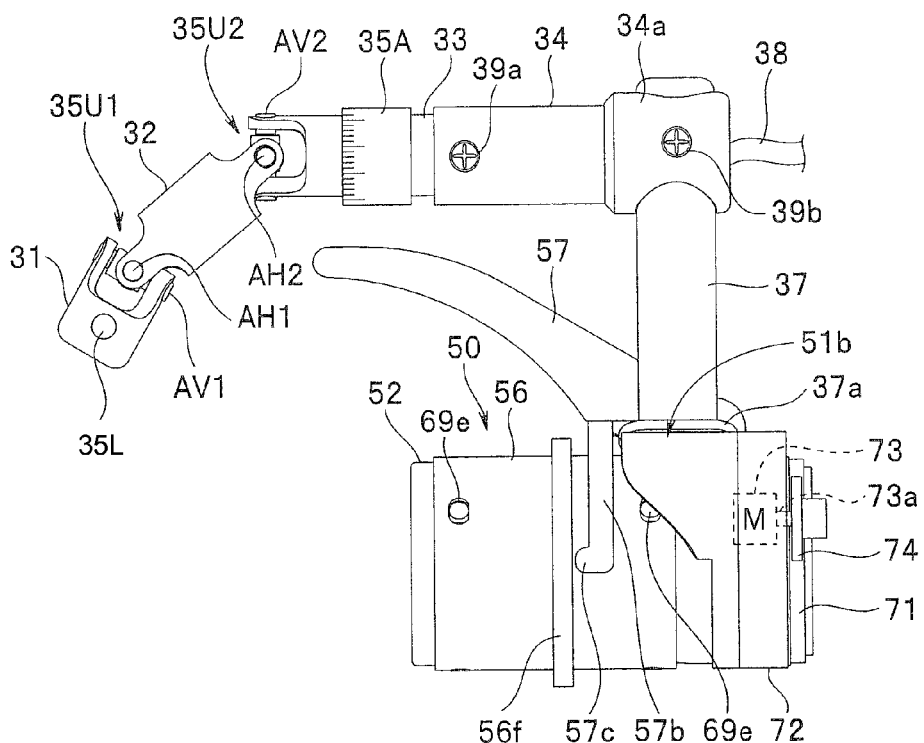
FIG. 11 shows a variant of an electric bending operation device, and illustrates an electric bending operation device with a different configuration and a different placement position of a twisting operation portion.

In the above described embodiment, the twisting operation portion 35 is provided on the distal end side of the first rod 31. However, as shown in FIG. 11, a twisting operation portion 35A may be provided on the fixing rod 33. With the configuration, operation errors of the first rod 31 or the like during the operation of the twisting operation portion 35 can be reliably prevented.

In the above described embodiment, the twisting operation portion 35 is the twisting detection encoder. However, a button 35L for indicating the twisting direction as shown in FIG. 11 and an unshown button 35R may be provided, for example, at the distal end portion of the first rod 31. With the configuration, the insertion portion 11 can be twisted while the button 35R or the button 35L is operated. In FIG. 11, the same components as in the configuration in FIG. 3 or the like for describing the embodiment are denoted by the same reference numerals, and descriptions thereof are omitted.

Figure 12:
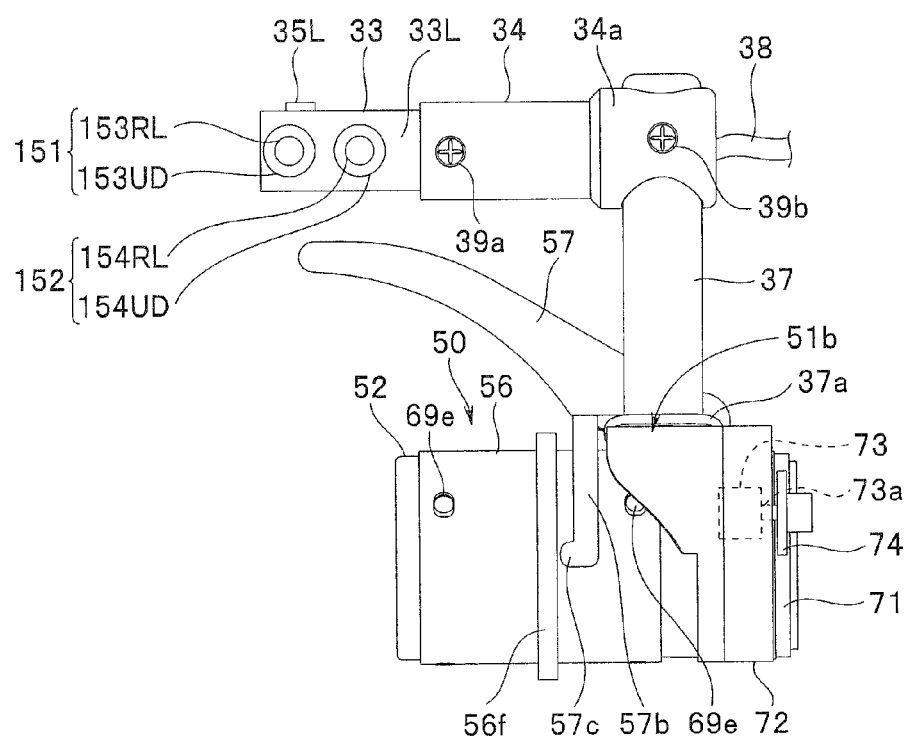
FIG. 12 shows a variant of an electric bending operation device, and illustrates an electric bending operation device with a different configuration of a bending portion operation section.

Also, as shown in FIG. 12, the electric bending operation device 5 may be configured so that knobs similar to the first vertically bending knob 23UD and the first laterally bending knob 23RL of the first bending portion operation section 21, and the second vertically bending knob 24UD and the second laterally bending knob 24RL of the second bending portion operation section 22 provided in the operation portion 12 of the endoscope 2 are provided, for example, on a left side surface 33L of the fixing rod 33, and the button 35L for indicating the twisting direction and the unshown button 35R are provided in line in the Y direction on an upper surface.

The knobs provided on the left side surface 33L are a first vertically bending knob 153UD and a first laterally bending knob 153RL that constitute a first bending portion operation section 151, and a second vertically bending knob 154UD and a second laterally bending knob 154RL that constitute a second bending portion operation section 152. With the configuration, perceiving the bending shape of the electric bending portion 15 appears difficult unlike the electric bending operation device 5 including the rods 31 and 32, but the size of the electric bending operation device can be further reduced without loss of the function of twisting the insertion portion 11.

Further, in the above described embodiment, the rotation driving force of the insertion portion rotation motor 73 is transmitted to the cylinder side spur gear 71a via the motor side spur gear 74 to rotate the rotary cylinder 52. However, the configuration for rotating the rotary cylinder 52 is not limited thereto, but may be a configuration in FIG. 13 or a configuration in FIG. 14.

Figure 13:
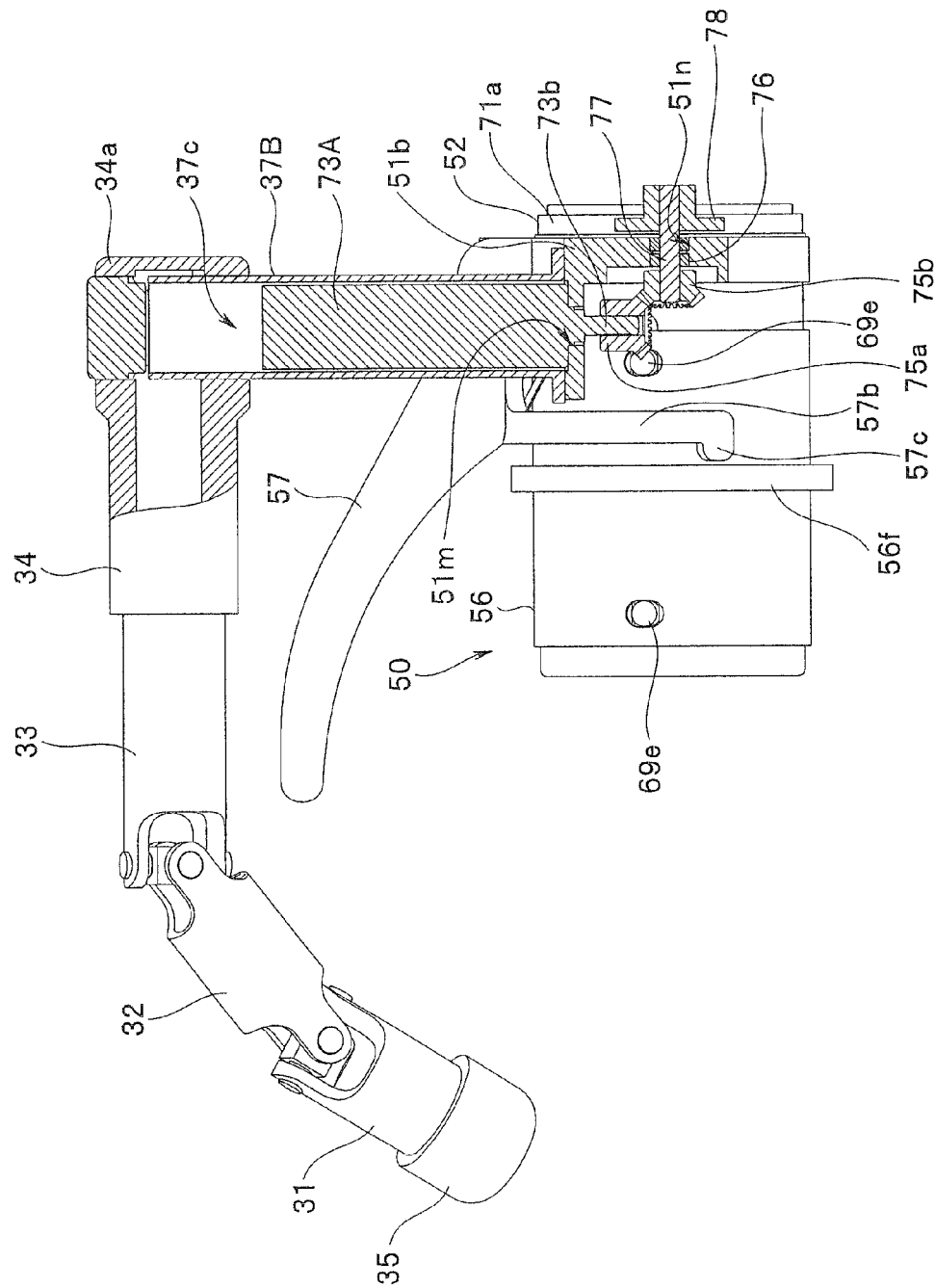
FIG. 13 illustrates an electric bending operation device with different configurations of an insertion portion rotation motor and a rotary cylinder.

With reference to FIG. 13, further exemplary configurations of an insertion portion rotation motor and a rotary cylinder will be described.

As shown in FIG. 13, in the present embodiment, an insertion portion rotation motor 73A is provided in an inner space 37c of a support column 37B. In a rotary cylinder 52, a cylinder side spur gear 71a as a cylinder gear 71 is provided. In the present embodiment, a support column mounting portion 51b has a motor shaft hole 51m through which a motor shaft 73a of the insertion portion rotation motor 73A passes. The motor shaft hole 5μm is a through hole that provides communication between a front surface and a back surface of the support column mounting portion 51b. To the motor shaft 73a, a first bevel gear 75a is integrally secured. The first bevel gear 75a is placed on a back surface side of the support column mounting portion 51b.

The support column mounting portion 51b has a through hole 51n in which a bearing 76 is provided. The bearing 76 rotatably supports a transmission shaft 77. The transmission shaft 77 includes, at one end, a second bevel gear 75b that meshes with the first bevel gear 75a, and at the other end, a spur gear 78 that meshes with the cylinder side spur gear 71a of the cylinder gear 71.

With the configuration, the insertion portion rotation motor 73A is driven to rotate the motor shaft 73a, and the rotation of the motor shaft 73a is transmitted to the cylinder gear 71 via the bevel gears 75a and 75b, the transmission shaft 77, and the spur gear 78 to rotate the rotary cylinder 52.

With the configuration, the insertion portion rotation motor 73A is provided in a support column 37B that constitutes the electric bending operation device 5, thereby eliminating the need for a motor housing 72, and reducing the size of the electric bending operation device 5. In FIG. 13, the same components as in the configuration in FIG. 3 or the like for describing the embodiment are denoted by the same reference numerals, and descriptions thereof are omitted.

Figure 14:
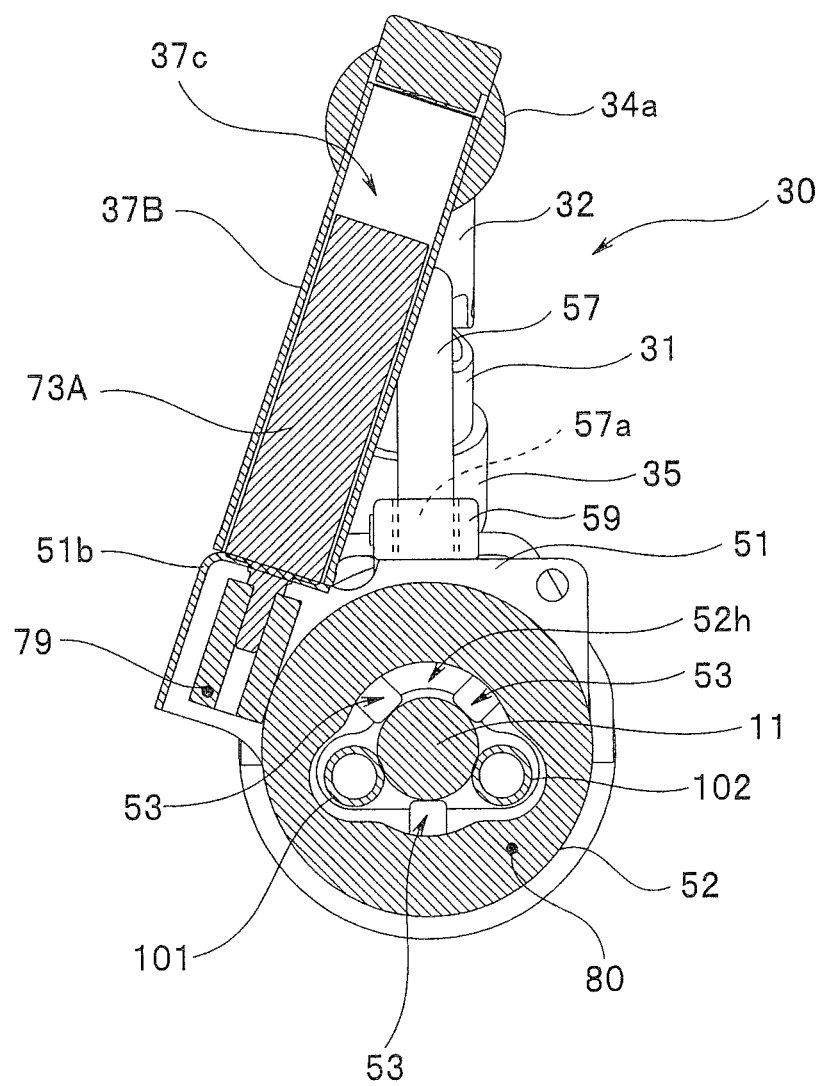
FIG. 14 illustrates an electric bending operation device with further different configurations of an insertion portion rotation motor and a rotary cylinder.

With reference to FIG. 14, further exemplary configurations of an insertion portion rotation motor and a rotary cylinder will be described.

As shown in FIG. 14, in the present embodiment, a worm gear 79 is secured to a motor shaft 73a of an insertion portion rotation motor 73A. A rotating portion 52a of a rotary cylinder 52 is a worm wheel 80 with which the worm gear 79 meshes. In FIG. 14, the same components as in the configuration in FIG. 5 or the like for describing the embodiment are denoted by the same reference numerals, and descriptions thereof are omitted.

With the configuration, rotation of the insertion portion 11 caused by a twisting reaction from the insertion portion 11 can be prevented besides the above described operations and advantages.

The external tubes 101 and 102 provided in the insertion portion 11 are generally made of flexible resin or rubber. However, the external tubes 101 and 102 may be formed of coil pipes having flexibility and rigidity against an external force.

With the configuration, the pressing portions 53a can press the external tubes 101 and 102 besides the insertion portion 11 to achieve firm securing. Also, instead of forming pressing portions that match respective different combinations of the outer diameter of the insertion portion 11 and outer diameters of the coil pipes, pawl members having wide pressing portions that accommodate various combinations can be provided in protrusions 52c and 52d, thereby reducing cost of the electric bending operation device 5.

In the above described embodiment, the medical instrument for observation is the electric bending endoscope, but the medical instrument for observation is not limited to the electric bending endoscope, but may be, for example, a medical tube including an electric bending portion similar to that of the above described electric endoscope. This medical tube is a so-called external tube having channel holes through which an observation probe, an illumination probe, and a manipulator are passed, in which a channel hole through which an endoscope is passed is provided instead of the channel holes through which the observation probe and the illumination probe are passed.

Figure 15:
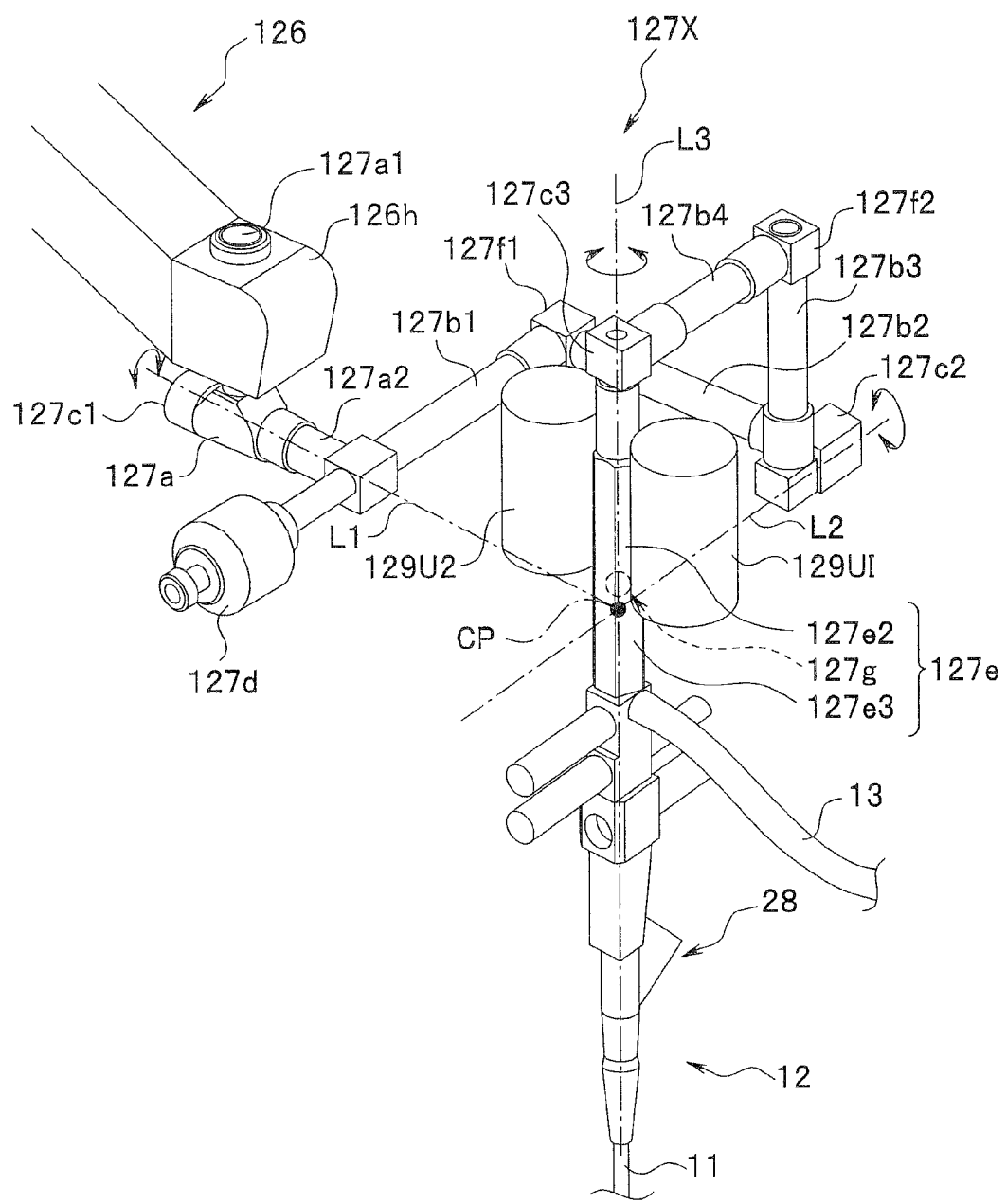
FIG. 15 illustrates a configuration of a scope holder including a ball joint in a securing portion.
Figure 16:
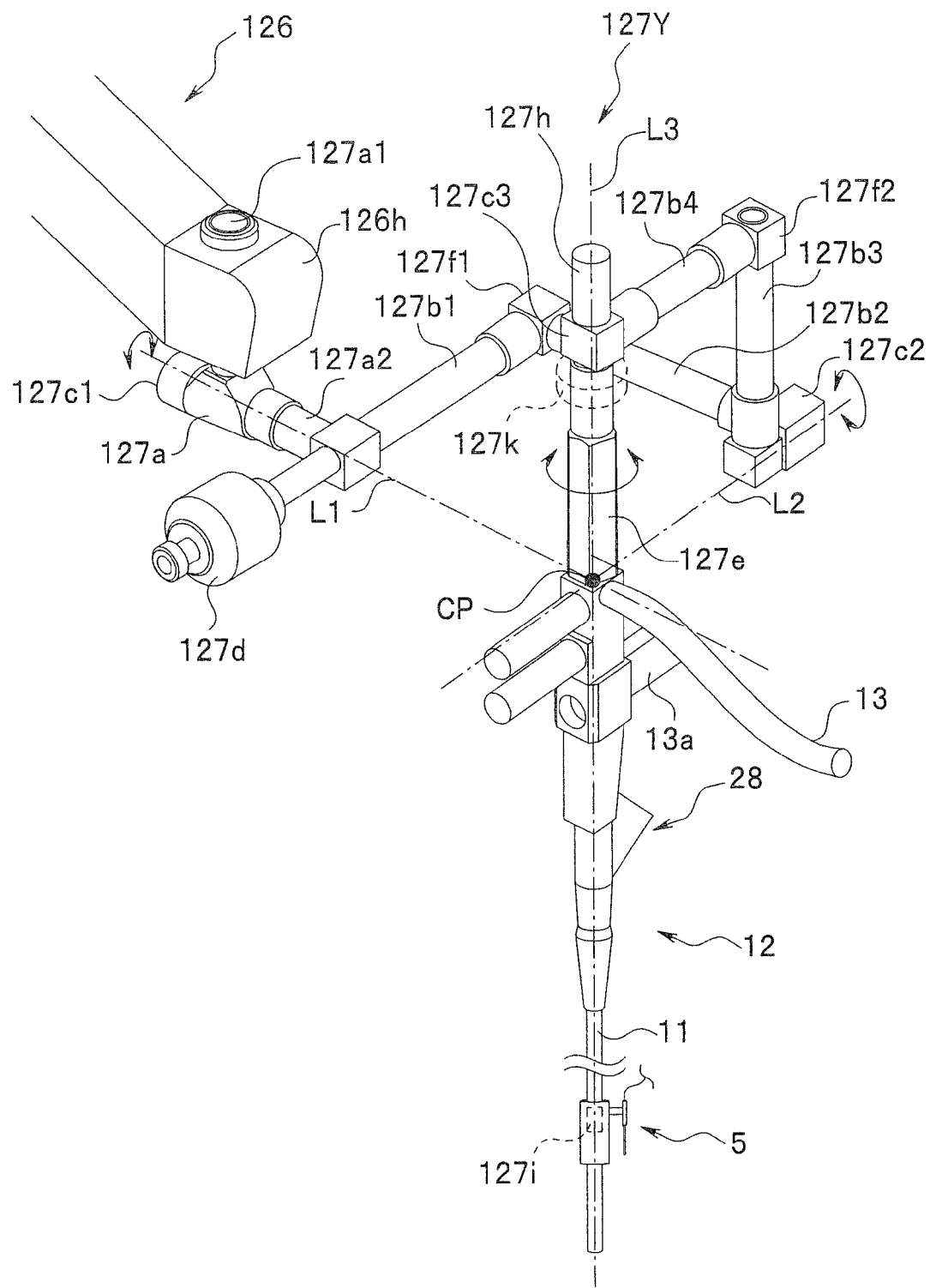
FIG. 16 illustrates a configuration of a scope holder including an endoscope rotation motor provided in a third rotational joint.

With reference to FIGS. 15 and 16, another exemplary configuration of the scope holder 127 will be described.

In a scope holder 127X in the present embodiment shown in FIG. 15, a securing portion 127e includes a first mounting member 127e2 and a second mounting member 127e3. The first mounting member 127e2 and the second mounting member 127e3 are connected by a ball joint 127g.

With the configuration, the flexibility of the scope holder 127X is increased, and thus when an operator operates a twisting operation portion 35 of an electric bending operation device 5, an operation portion 12 is also twisted to allow smooth twisting operation of the insertion portion 11.

In the drawing, the center of the ball joint 127g is placed close to the above described crosspoint CP. Thus, though not shown, a distal end side from an extending portion 13a of a universal cord 13 is secured in the vicinity of the crosspoint CP.

In a scope holder 127Y in the present embodiment shown in FIG. 16, an endoscope rotation motor 127h is provided in a third rotational joint 127c3. The endoscope rotation motor 127h rotates a securing portion 127e rotatably mounted to the third rotational joint 127c3. In the present embodiment, the electric bending operation device 5 includes a rotation operation force amount detection sensor 127i that detects the amount of rotation operation of the insertion portion 11 rotated with rotation of the rotary cylinder 52.

The endoscope rotation motor 127h is driven on the basis of rotation detection signals outputted from the rotation operation force amount detection sensor 127i to an endoscope control device 3. Specifically, simultaneously with an input of a rotation detection signal, the endoscope control device 3 compares the signal with a threshold, and determines whether the endoscope rotation motor 127h is driven or determines an output value of a driving force.

Then, the endoscope control device 3 outputs a predetermined rotation control signal to the endoscope rotation motor 127h when the endoscope rotation motor 127h is driven. Then, the driving of the endoscope rotation motor 127h rotates the securing portion 127e to rotate the operation portion 12 of the electric bending endoscope 2.

With the configuration, the endoscope rotation motor 127h provided in the scope holder 127Y is operated on the basis of the rotation detection signal outputted from the rotation operation force amount detection sensor 127i of the electric bending operation device 5. Thus, when the operator operates the twisting operation portion 35, the endoscope rotation motor 127h assists the twisting operation of the insertion portion 11 as required to allow stable twisting operation of the insertion portion 11 to be always performed. This can reduce the size of the insertion portion rotation motor 73.

Instead of providing the rotation operation force amount detection sensor in the electric bending operation device 5, a torque sensor 127k that detects rotation of the operation portion 12 of the electric bending endoscope 2 may be provided as shown by the broken line in the drawing. With the configuration, the endoscope rotation motor 127h is driven on the basis of a torque detection signal outputted from the torque sensor 127k, and assists the twisting operation of the insertion portion 11.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric bending operation device, comprising:
an insertion portion mounting mechanism that includes an insertion portion pressing member that is provided integrally with a rotary cylinder through which an insertion portion of a medical instrument for observation including an electric bending portion is passed and presses and holds the insertion portion, and can be switched between a state where the insertion portion pressing member is pressed against the insertion portion and the rotary cylinder is integral with the insertion portion and a state where the insertion portion is advanced or retracted with respect to the rotary cylinder;

a rotation mechanism that is provided in the insertion portion mounting mechanism, and rotates the rotary cylinder to rotate the insertion portion around an axis thereof when the rotary cylinder is integral with the insertion portion;

an insertion portion operation section including a bending portion operation section that performs bending operation of the electric bending portion provided in the insertion portion, and a twisting operation portion that rotates the rotary cylinder; and a support column that integrally connects the insertion portion operation section and the insertion portion mounting mechanism;

wherein the insertion portion mounting mechanism includes:

an annular device body;

the rotary cylinder rotatably held in an inner peripheral surface of the device body, and through which the insertion portion is passed;

a protrusion that is integrally provided on an inner surface of the rotary cylinder, includes a through hole through which the insertion portion passes, and rotatably includes the insertion portion pressing member that is placed in the through hole and includes a pressing portion that presses at least an outer surface of the insertion portion;

a switching cylinder that is slidably placed in the rotary cylinder, has a press hole in which the pressing portion of the insertion portion pressing member is placed, and slides in the rotary cylinder to switch between a state where the pressing portion presses the outer surface of the insertion portion and a state where the pressing portion does not press the outer surface of the insertion portion;

a biasing member that is placed in the rotary cylinder, biases the switching cylinder in an extended state, and causes the pressing portion placed in the press hole in the switching cylinder to press against the outer surface of the insertion portion;

a movable cylinder that is slidably placed on an outer peripheral surface of the rotary cylinder, and formed integrally with the switching cylinder; and a lever that is rotatably placed on the device body, moves the movable cylinder in a longitudinal axis direction of the rotary cylinder against a biasing force of the biasing member, and releases a pressing state of the pressing portion against the outer surface of the insertion portion by the biasing force of the biasing member.

2. The electric bending operation device according to claim 1, wherein the rotation mechanism includes:

an annular device body;

a rotary cylinder rotatably held in an inner peripheral surface of the device body, through which the insertion portion is passed; and having a cylinder gear;

an insertion portion rotation motor that is directly or indirectly secured to the device body, and generates a rotating force for rotating the rotary cylinder;

and a gear train that transmits the rotating force of the insertion portion rotation motor to the rotary cylinder.

3. The electric bending operation device according to claim 2, wherein the insertion portion rotation motor is provided in a motor housing secured to the device body, and gears that constitute the gear train are spur gears.

4. The electric bending operation device according to claim 2, wherein the insertion portion rotation motor is provided in an inner space of the support column, and the gears that constitute the gear train include bevel gears or worm gears.

5. The electric bending operation device according to claim 1, wherein the bending portion operation section of the insertion portion operation section is a bendable rod including a universal joint, and the twisting operation portion rotates around an axis of the rod or an axis of the insertion portion operation section.

6. An electric bending operation device, comprising:

an annular device body;

a rotary cylinder rotatably held in an inner peripheral surface of the device body, and through which an insertion portion including an electric bending portion provided in a medical instrument for observation is passed;

an insertion portion pressing member that is placed on an inner surface of the rotary cylinder, and presses an outer surface of the insertion portion to switch between a state where the insertion portion is integral with the rotary cylinder and a state where the insertion portion is advanced or retracted with respect to the rotary cylinder;

a switching mechanism including a lever that switches between a state where the insertion portion pressing member is pressed against the insertion portion and the insertion portion is integral with the rotary cylinder and a state where the insertion portion is advanced or retracted with respect to the rotary cylinder;

an insertion portion rotation motor that is secured to the device body and rotates the rotary cylinder;

an insertion portion operation section including an operation portion support member that is secured to a support column standing on the device body and also serves as a grasping portion having a longitudinal axis parallel to a longitudinal axis of the rotary cylinder, and a bending portion operation section that bends an electric bending portion provided in the insertion portion and a twisting operation portion that rotates the rotary cylinder, mounted to the operation portion support member; and a support column that integrally connects the insertion portion operation section and the device body;

wherein the switching mechanism includes:

a protrusion that is provided integrally on the inner surface of the rotary cylinder, and rotatably includes the insertion portion pressing member including a pressing portion that presses the outer surface of the insertion portion;

a switching cylinder that is slidably placed in the rotary cylinder, has a press hole in which the pressing portion of the insertion portion pressing member is placed, and slides in the rotary cylinder to switch between a state where the pressing portion presses the outer surface of the insertion portion and a state where the pressing portion does not press the outer surface of the insertion portion;

a biasing member that is placed in the rotary cylinder, biases the switching cylinder in an extended state, and causes the pressing portion placed in the press hole in the switching cylinder to press against the outer surface of the insertion portion;

a movable cylinder that is slidably placed on an outer peripheral surface of the rotary cylinder, and formed integrally with the switching cylinder slidable in the rotary cylinder; and a lever that is rotatably placed in the device body, moves the movable cylinder in a longitudinal axis direction of the rotary cylinder against a biasing force of the biasing member, and releases a pressing state of the pressing portion against the outer surface of the insertion portion by the biasing force of the biasing member.

7. The electric bending operation device according to claim 6, wherein the center of gravity of the electric bending operation device is provided in a plane including the lever and the operation portion support member of the insertion portion operation section secured to the support column.

8. The electric bending operation device according to claim 6, wherein the bending portion operation section of the insertion portion operation section is a bendable rod including a universal joint, and the twisting operation portion rotates around an axis of the rod or an axis of the insertion portion operation section.

* * * * *